United States Patent
Celedon et al.

(10) Patent No.: US 8,350,564 B2
(45) Date of Patent: Jan. 8, 2013

(54) MAGNETIC TWEEZERS METHOD TO MEASURE SINGLE MOLECULE TORQUE

(75) Inventors: Alfredo A. Celedon, Baltimore, MD (US); Sean X. Sun, Baltimore, MD (US); Gregory Bowman, Pikesville, MD (US); Denis Wirtz, Washington, DC (US); Peter Searson, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 494 days.

(21) Appl. No.: 12/720,025

(22) Filed: Mar. 9, 2010

(65) Prior Publication Data

US 2010/0253328 A1 Oct. 7, 2010

Related U.S. Application Data

(60) Provisional application No. 61/159,006, filed on Mar. 10, 2009, provisional application No. 61/158,507, filed on Mar. 9, 2009.

(51) Int. Cl.
G01R 33/00 (2006.01)
G01R 33/02 (2006.01)
G01R 33/12 (2006.01)

(52) U.S. Cl. ........ 324/244; 324/228; 324/262; 977/849; 435/287.1

(58) Field of Classification Search .................. 324/244, 324/228, 262; 435/287.1; 977/849
See application file for complete search history.

(56) References Cited

U.S. PATENT DOCUMENTS
2010/0253328 A1 10/2010 Celedon et al.

OTHER PUBLICATIONS

Charvin et al., *Tracking Topoisomerase Activity at the Single-Molecule Level*, Annu. Rev. Biophys. Biomol. Struct. 34, pp. 201-219 & C1-C4 & Table of Contents (2 pages), 2005.

Peter et al., *"Genomic transcriptional response to loss of chromosomal supercoiling in Escherichia coli,"* Genome Biology, 5(11), pp. 1-16, 2004.

Koster et al., *"Friction and torque govern the relaxation of DNA supercoils by eukaryotic topoisomerase IB,"* Nature 434, pp. 671-674, 2005.

R. Metzler et al., *"Single DNA conformations and biological function,"* Comp. & Theor. Nanosci. 4, 1-49, 2007; arXiv:physics/0609139, 2, pp. 1-53, 2006.

Kouzine et al., *"The functional response of upstream DNA to dynamic supercoiling in vivo,"* Nature Structural & Molecular Biology, 15(2), pp. 146-154, 2008.

Liu et al., *"Supercoiling of the DNA template during transcription,"* Proc. Natl. Acad. Sci., vol. 84, pp. 7024-7027, 1987.

Koster et al., *Antitumour drugs impede DNA uncoiling by topoisonmerase I*, Nature, 448, pp. 213-217, 2007; doi:10.1038/nature 05938.

Pomerantz et al., *"A Tightly Regulated Molecular Motor Based upon T7 RNA Polymerase,"* Nano Letters, 5(9), pp. 1698-1703, 2005.

Bancaud et al., *Structural plasticity of single chromtin fibers revealed by torsional manipulation*, Nature Structural & Molecular Biology, 13(5), pp. 444-450, 2006.

Forth et al., *"Abrupt Buckling Transition Observed during the Plectoneme Formation of Individual DNA Molecules,"* Physical Review Letters, 100, pp. (148301) 1-(148301) 4, Apr. 11, 2008.

(Continued)

*Primary Examiner* — Reena Aurora
(74) *Attorney, Agent, or Firm* — Venable LLP; Henry J. Daley; Lars H. Genieser

(57) ABSTRACT

A system and a method for determining the torque imposed on a filament, such as a single DNA strand or macromolecule, using a magnetic probe and an imaging device.

21 Claims, 14 Drawing Sheets

OTHER PUBLICATIONS

Deufel et al., "*Nanofabricated quartz cylinders for angular trapping: DNA supercoiling torque detection,*" Nature Methods, 4(3), 2007, pp. 223-225.

Oroszi et al., "*Direct Measure of Torque in an Optical Trap and Its Application to Double-Strand DNA,*" Physical Review Letters, 97, pp. (058301) 1-(058301) 4, Aug. 4, 2006.

Bryant et al., "*Structural transitions and elasticity from torque measurements on DNA,*" Nature, 424, pp. 338-341, 2003.

Strick et al., "*The Elasticity of a Single Supercoiled DNA Molecule,*" Science, 271, pp. 1835-1837, 1996.

Haber et al., "*Magnetic tweezers for DNA,*" Review of Scientific Instruments 71(12), pp. 4561-4570, 2000.

Leuba et al., "*Assembly of single chromatin fibers depends on the tension in the DNA molecule: Magnetic tweezers study,*" PNAS, 100(2), pp. 495-500, 2003.

Bancaud et al., "*Nucleosome Chiral Transition under Positive Torsional Stress in Single Chromatin Fibers,* " Molecular Cell, 27, pp. 135-147, 2007.

Yan et al., "*Micromanipulation Studies of Chromatin Fibers in Xenopus Egg Extracts Reveal ATP-dependent Chromatin Assembly Dynamics,*" Molecular Biology of the Cell, 18, pp. 464-474, 2007.

Charvin et al., *Tracking Topoisomerase Activity at the Single-Molecule Level*, Annu. Rev. Biophys. Biomol. Struct. 34, pp. 201-219, 2005.

Gore et al., "*Mechanochemical analysis of DNA gyrase using rotor bead tracking,*" Nature, 439, pp. 100-104, 2006.

Revyakin et al., "*Promoter unwinding and promoter clearance by RNA polymerase: Detection by single-molecule DNA nanomanipulation,*" PNAS, 101(14), pp. 4776-4780, 2004.

Revyakin et al., "*Abortive Initiation and Productive Initiation by RNA Polymerase Involve DNA Scrunching,*" Science, 314, pp. 1139-1143 & Title Sheet, 2006.

Lia et al., "*The antiparallel loops in gal DNA,*" Nucleic Acids Research, 36(12), pp. 4204-4210, 2008.

Whitney et al., "*Fabrication and Magnetic Properties of Arrays of Metallic Nanowires,*" Science, 261, pp. 1316-1319, 1993.

Gosse et al., "*Magnetic Tweezers: Micromanipulation and Force Measurement at the Molecular Level,*" Biophysical Journal, 82, pp. 3314-3329, 2002.

Chen et al., "*Potential Modulated Multilayer Deposition of Multisegment Cu/Ni Nanowires with Tunable Magnetic Properties,*" Chem. Mater., 18, pp. 1595-1601, 2006.

Marko, "*Torque and dynamics of linking number relaxation in stretched supercoiled DNA,*" Physical Review E, 76, pp. (021926) 1-(021926) 13, 2007.

Strick et al., "*Behavior of Supercoiled DNA,*" Biophysical Journal, 74, pp. 2016-2028, 1998.

PicoTwist, "*Magnetic Tweezers,*" http://www.picotwist.com/index.php?content=smb&option=mag (accessed Feb. 26, 2010).

MAGNETIC TWEEZERS METHOD TO MEASURE SINGLE MOLECULE TORQUE

This application claims the benefit of U.S. Provisional Application No. 61/158,507, filed Mar. 9, 2009, and of U.S. Provisional Application No. 61/159,006, filed Mar. 10, 2009, which are hereby incorporated by reference in their entirety.

The present invention pertains to the measurement of torque imposed on a filament, such as a single DNA macromolecule in a duplex or double-stranded helical configuration.

This invention was made with Government support under Grant No. CMS-0528296 awarded by the National Institutes of Health. The Government has certain rights in this invention.

SUMMARY OF THE INVENTION

In an embodiment according to the invention, a system includes a translation stage, a substrate having a first binding point suitable for attachment of a first end of a filament, a magnet opposite of the substrate, a magnetic probe having a magnetic moment, an azimuthal orientation, and a second binding point suitable for attachment of a second end of the filament, positioned between the substrate and the magnet, and an imaging device near to the substrate, magnet, and magnetic probe. A translation stage can be attached to the substrate. A translation stage can be attached to the magnet. The imaging device can determine the azimuthal orientation of the magnetic probe. The second binding point of the magnetic probe can be offset from the magnetic moment.

In an embodiment, the magnetic moment of the magnetic probe is approximately parallel to an orientation axis passing through the first binding point and the second binding point. The translation stage can have 2 axes of motion. The magnet can be a single permanent magnet. The single permanent magnet can be affixed to a z-stage translatable in a direction approximately parallel to the orientation axis. The magnet can be an electromagnet, and can have a variable magnetic field. The magnetic probe can include a magnetic bead and a lever. The magnetic moment of the magnetic probe can pass through the magnetic bead. The lever can include the second binding point. The magnetic probe can include a superparamagnetic material. The filament can include a macromolecule.

A method for determining the torque applied to a filament according to the invention includes affixing a first end of the filament to a substrate, affixing a second end of the filament to a magnetic probe having an azimuthal orientation, applying an external magnetic field having a magnetic axis to move the magnetic probe and elongate the filament along an orientation axis passing through the first end and the second end of the filament, translating the first end of the filament relative to the magnetic axis (for example, by translating the substrate and/or the magnetic field) to change the azimuthal orientation of the magnetic probe and impose twist on the filament, obtaining images of the magnetic probe at a plurality of successive times, using the images to determine the azimuthal orientation of the magnetic probe at the successive times, obtaining a probability distribution of azimuthal orientations from the azimuthal orientations at the successive times, and determining the torque on the filament from the probability distribution of azimuthal orientations. The filament can be a polynucleotide. The substrate can be translated in a curve having a winding number about the magnetic probe. The winding number can be fractional, for example, one-half (0.5) revolution or one and one half (1.5) revolutions. The torque on the filament as a function of the azimuthal orientation and/or the winding number can be determined. The external magnetic field can be varied to vary an elongation force along the orientation axis of the filament. The torque as a function of the elongation force and the azimuthal orientation and/or the winding number can be varied.

BRIEF DESCRIPTION OF THE DRAWINGS

FIG. 1a illustrates how the magnetic field created by a cylindrical magnet is used to manipulate a magnetic probe attached to the molecule under study. FIG. 1b presents a top view of the system. FIG. 1c presents a view of the system including the imaging device and the z-translational stage for moving the cylindrical magnet toward and away from the probe.

FIG. 5a: Chromatin was generated from the same DNA used for bare DNA experiments described in FIG. 4. The turn-vs-extension and turn-vs-torque curves at 0.3 pN pulling force are shown for three molecules. FIG. 5b: Extension and torque hysteresis was observed in the chromatin fibers. Two consecutive loops are shown for a single molecule.

DETAILED DESCRIPTION

Figure 1:
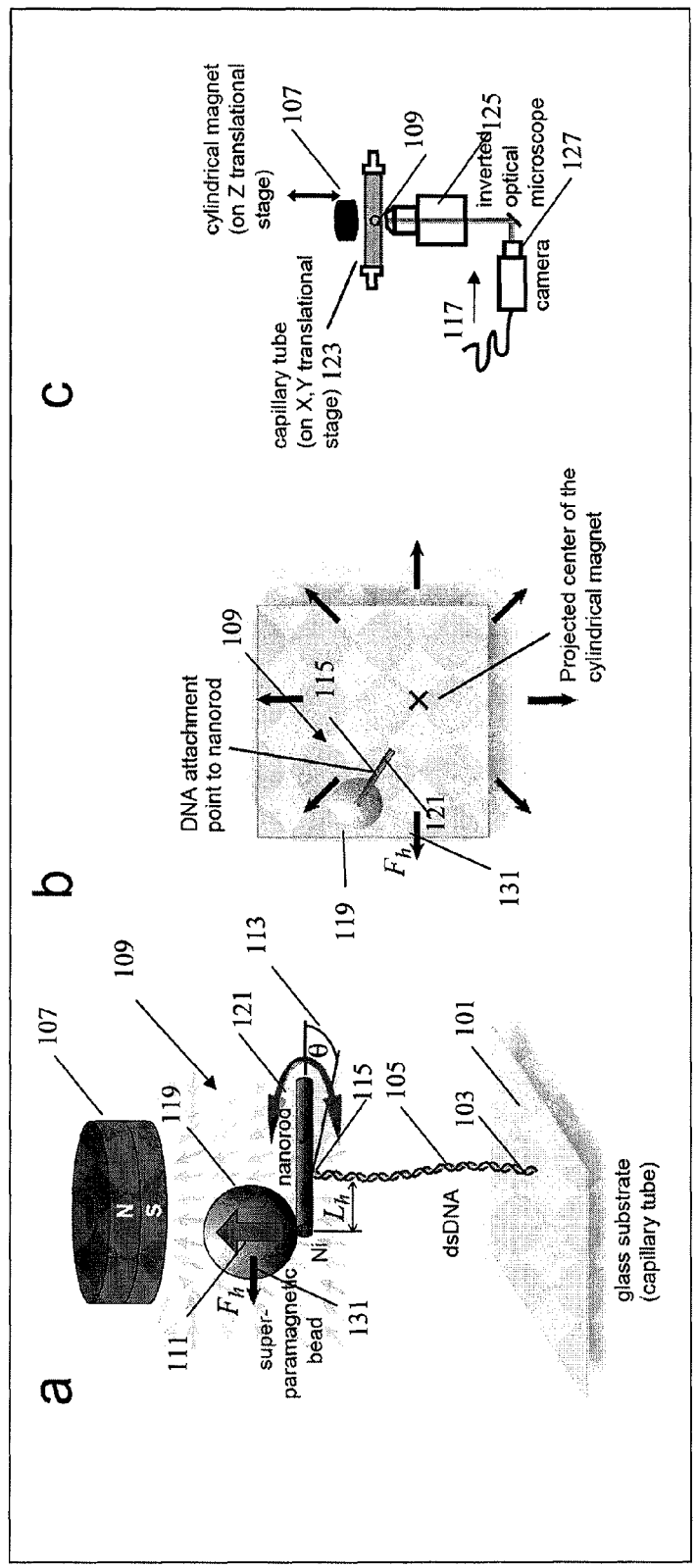
FIGS. 1a-1c present a system for single molecule torque measurement.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without parting from the spirit and scope of the invention. All references cited herein are incorporated by reference as if each had been individually incorporated.

Torsional stress in linear biopolymers such as DNA and chromatin has important consequences for nanoscale biological processes. We have developed a new method to directly measure torque on single molecules. Using a cylindrical magnet, we manipulate a novel probe consisting of a nanorod with a 0.1 µm ferromagnetic segment coupled to a magnetic bead according to an embodiment of the current invention. We achieve controlled introduction of turns into the molecule, precise measurement of torque and molecule extension as a function of the number of turns at low pulling force. We show torque measurement of single DNA molecules and demonstrate for the first time measurements of single chromatin fibers.

DNA and other linear biopolymers accumulate torsional stress under the action of a rotary force or torque. This property has important biological implications, for example, torsional stress affects the action of enzymes that act on DNA.[1-3] Fundamental biological processes such as DNA replication and transcription involve biological nanomachines that exert torque on double stranded (ds) DNA and chromatin.[4,5] Thus, in order to reveal the mechanisms and energetics of these processes, it is imperative to have tools to measure the torque required to twist linear biopolymers, such as DNA and chromatin. Understanding how biological processes and linear biopolymers are affected by torsional stress is important in the design of chemotherapeutic drugs,[6] and applications involving DNA biological machines.[7] Moreover, the ability to measure the torque of single molecules is important in understanding molecular structure, such as the chromatin structure;[8] and, in general, an essential tool to study the torsional properties of nanoscale linear biopolymers.

The dependence of torque on twist for DNA has been measured with optical angular trapping methods,[9-11] and has been analyzed from viscous drag forces.[12] However, like other biopolymers, the structure of DNA is sensitive to pulling force, and these techniques employ pulling forces greater than 1 pN, sufficient for melting duplex DNA when negative twists are introduced. DNA and chromatin in vivo are usually free from stretching forces and hence it is of fundamental interest to study these filaments or fibers using a device that can measure torque at low pulling force. Twisting a single molecule at low pulling force can be achieved using magnetic tweezers. Magnetic tweezers techniques have been used to study naked DNA,[13,14] chromatin,[8,15-17] and enzymes that act on DNA.[2,18-22] The conventional magnetic tweezers setup, however, does not allow measuring single molecule torques (~10 pN·nm [ref.[9]]) because, as we show below, they do not produce a measurable change in the angular orientation of the probe used to twist the molecule.

To allow measurement of torque at low pulling forces (0.1-1.5 pN), we have developed a new magnetic tweezers configuration (FIG. 1). We use a probe consisting of a 2 µm long and 0.2 µm diameter Ni—Pt nanorod with a 0.1 µm Ni segment, produced by electrochemical template synthesis,[23] coupled to a 1 µm diameter superparamagnetic bead according to an embodiment of the current invention. This probe is manipulated using a cylindrical magnet. The new device allows direct and precise torque measurement of single molecules. We use the new method to measure torque in single DNA molecules and for the first time present results for single chromatin fibers. Our bare DNA measurements match existing measurements at pulling forces>1 pN and agree with theoretical predictions at lower pulling forces. The results for chromatin show that the torsional rigidity of chromatin fibers is lower than naked DNA at the same pulling force.

In order to study the torsional properties of DNA and other linear biopolymers at low pulling force in a single molecule experiment, there are four main aspects. First, we can be able to introduce turns into the molecule. This can be accomplished by first linking one end of the molecule to the nanorod and the other end to the glass substrate, and then rotating the nanorod-bead probe. The probe can be rotated by exposing the probe to a rotating magnetic field. Second, we can be able to measure torque at any configuration (i.e., number of turns). This can be achieved in the following way. Under equilibrium conditions the magnetic field holds the probe at a given angular orientation but sufficiently weakly to allow thermal fluctuations. Torque can be calculated from the change in the angular distribution of the probe before and after introducing turns into the molecule. To do this, the probe can be confined in a weak trap, so that the orientational change can be observed. Third, we can measure the extension of the molecule perpendicular to the surface. This can be measured from analysis of the interference pattern from the bead attached to the nanorod[24]. Fourth, we can apply and measure a small vertical force. This force can be applied to the molecule through the probe and can be the result of a vertical gradient in the magnetic field. This force can keep the molecule extended and allow us to explore the influence of applied force on torque and on molecule extension. The vertical force can be measured from the fluctuations of the probe in the x-y plane.[13]

An embodiment of a system for single molecule torque measurement according to the present invention is presented in FIGS. 1a-1c. FIG. 1a illustrates how the external magnetic field created by a magnet 107 (in an embodiment a cylindrical permanent magnet) is used to manipulate a magnetic probe 109 attached to the filament 105 under study, such as a macromolecule or DNA double helical strand. Other types of magnet 107 can be used, for example, coils of wire through which an electric current flows can form an electromagnet that generates the magnetic field, the coils of wire can have an air-core or an iron core. Such an electromagnet used as the magnet 107 can be configured, so that the electric current through the coils, and, thus, the magnetic field generated, can be variable and under the control of a user. The magnetic probe 109 shown includes a Ni—Pt nanorod 121, which serves as a lever, coupled to a 1 µm magnetic bead 119. The magnetic bead can include, for example, a ferromagnetic material, a superparamagnetic material, and/or a material endowed with another magnetic property. One end of the filament 105 is attached to the glass substrate 101 at a first binding point 103 and the other end to the nanorod 121 at a second binding point 115 at a distance $L_h$ from the Ni segment. The magnetic field and the probe dipole 111 (arrow with color gradient) align vertically. A horizontal force $\vec{F}_h$ 131 (<0.1 pN), arising from a gradient in the magnetic field, produces a torque $\vec{L}_h \times \vec{F}_h$ which weakly traps the horizontal (azimuthal) angular fluctuations of the probe (fluctuations of the angle θ 113), allowing controlled twisting of the filament 105 and detection of the torque applied to the filament 105. An orientation axis can be defined as a line passing through the first binding point 103 and the second binding point 115. The magnetic moment 111 of the magnetic probe 109 can be approximately parallel (for example, parallel to within ±20°, ±15°, ±12°, ±10°, ±5°, ±4°, ±3°, ±2°, ±1°, ±0.6°, ±0.5°, ±0.2°, or ±0.1°). The azimuthal orientation or azimuthal angle θ (113) can be defined in a plane normal to orientation axis of the filament 105.

In an embodiment, the substrate 101 is glass, e.g., a glass capillary tube 123. However, the substrate can be formed of any other suitable material, such as a non-silica glass or a non-glass material.

The magnetic probe 109 formed from the magnetic bead 119 and the nanorod 121 is just one example of a magnetic probe 109 that can be used in an embodiment of a system according to the invention. For example, a magnetic probe 109 can include a single object, of which the second binding point 115 is offset from the magnetic moment 111. The magnetic probe 109 can have a nonspherical form and be aligned so that the imaging device can determine the azimuthal orientation of the magnetic probe 109. Alternatively, the magnetic probe can be marked (e.g., by a color or fluorescent marker) on different parts of its surface so that the imaging device can determine its azimuthal orientation even if its form appears symmetric (e.g., circular) to the imaging device.

Figure 10:
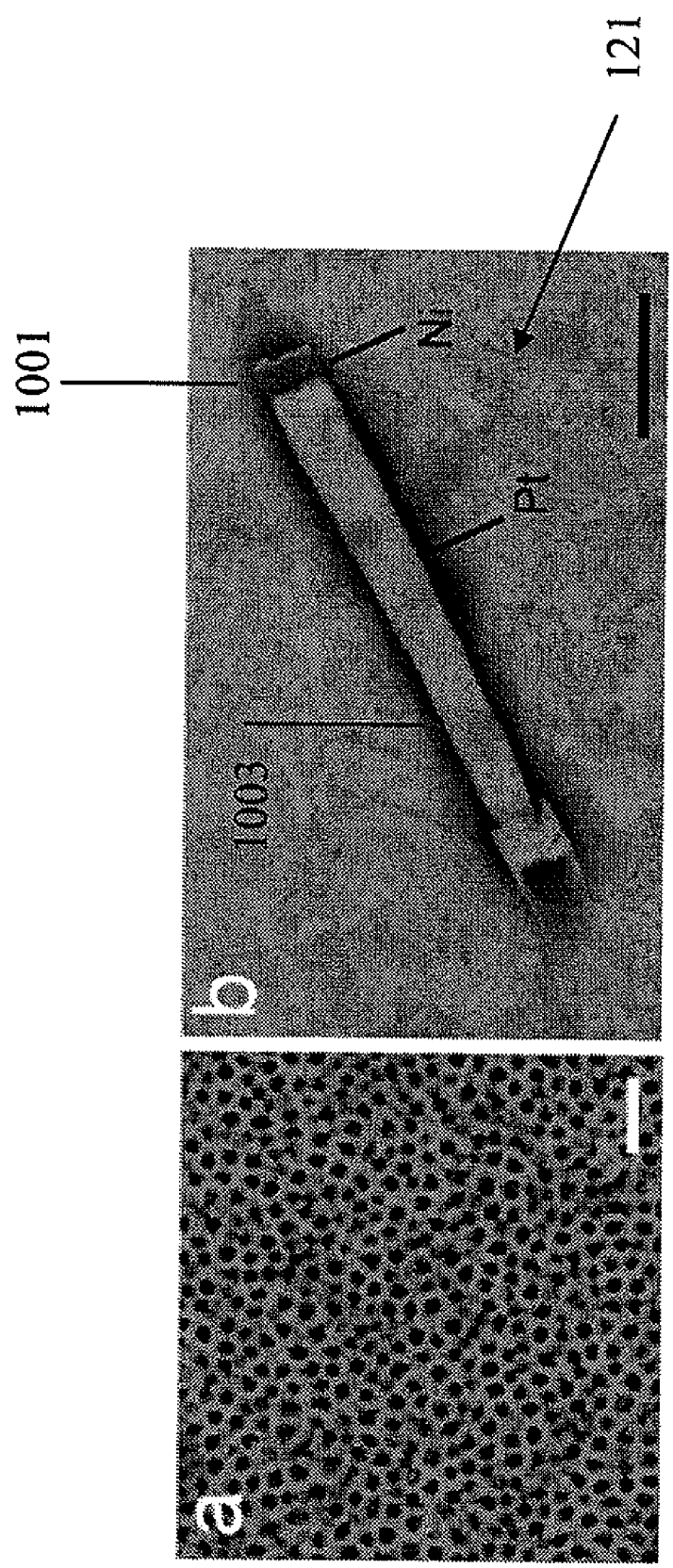
FIG. 10a shows a scanning electron micrograph of the aluminum oxide template used for nanorod electrodeposition.
FIG. 10b shows a scanning electron micrograph of a Ni—Pt nanorod (bar=0.5 µm).

The nanorod 121 can be formed of a nickel 1001 and a platinum 1003 segment as described (FIG. 10). Alternatively, the nanorod can be formed of other materials, for example, other metals. For example, a ferromagnetic material other than nickel can be used. For example, a non-ferromagnetic material other than platinum can be used.

The filament 105 under study can be, for example, a fiber, a structure containing multiple aligned macromolecules, a single DNA double helical structure having two polynucleotide strands, a single polynucleotide strand, or a single macromolecule, such as a polymer, or another structure, such as a carbon nanotube.

FIG. 1b presents a top view of the system. The horizontal force is symmetric around the axis of the cylindrical magnet 107 (broad arrows). The torque $\vec{L}_h \times \vec{F}_h$ orients the nanorod 121 in the direction of the force $\vec{F}_h$ 131. Controlled rotation of the magnetic probe 109 can be obtained by moving the glass capillary such that the probe follows a path around the projected center of the cylindrical magnet 107.

FIG. 1c presents a view of the system including the imaging device 117. A z-translational stage can move the cylindrical magnet 107 toward and away from the probe 109. Single molecule manipulation can take place inside a capillary tube 123 over an inverted optical microscope 125. Samples can be observed on an inverted microscope 125 (Nikon Eclipse, TE2000-E) using a 100× oil-immersion objective. The nosepiece of the microscope can be on a motorized z-stage which allows 50 nm steps. Video images can be obtained with a CCD digital camera 127 (Hamamatsu, ORCA-ER) connected to a PC computer. Video images can be analyzed in real time at 21 Hz using software written in MATLAB (version 7.6.0.324). The cylindrical magnet 107 can be held above the capillary by the z-translational linear stage.

Although FIGS. 1a and 1c show components in a certain orientation, for example, the magnet 107 above the substrate 101, it is to be understood throughout this application that it is the relative orientation of components, and not their absolute orientation, that is relevant to the system. For example, the magnet 107, the magnetic probe 109, and the filament 105 can be located below the substrate 101. For example, the magnet 107, the magnetic probe 109, and the filament 105 can be located to the side of a substrate 101. For example, in each of these configurations, the magnet 107 can be arranged in a relationship opposed to the substrate 101.

Controlled Introduction of Turns into the Molecule.

Figure 6:
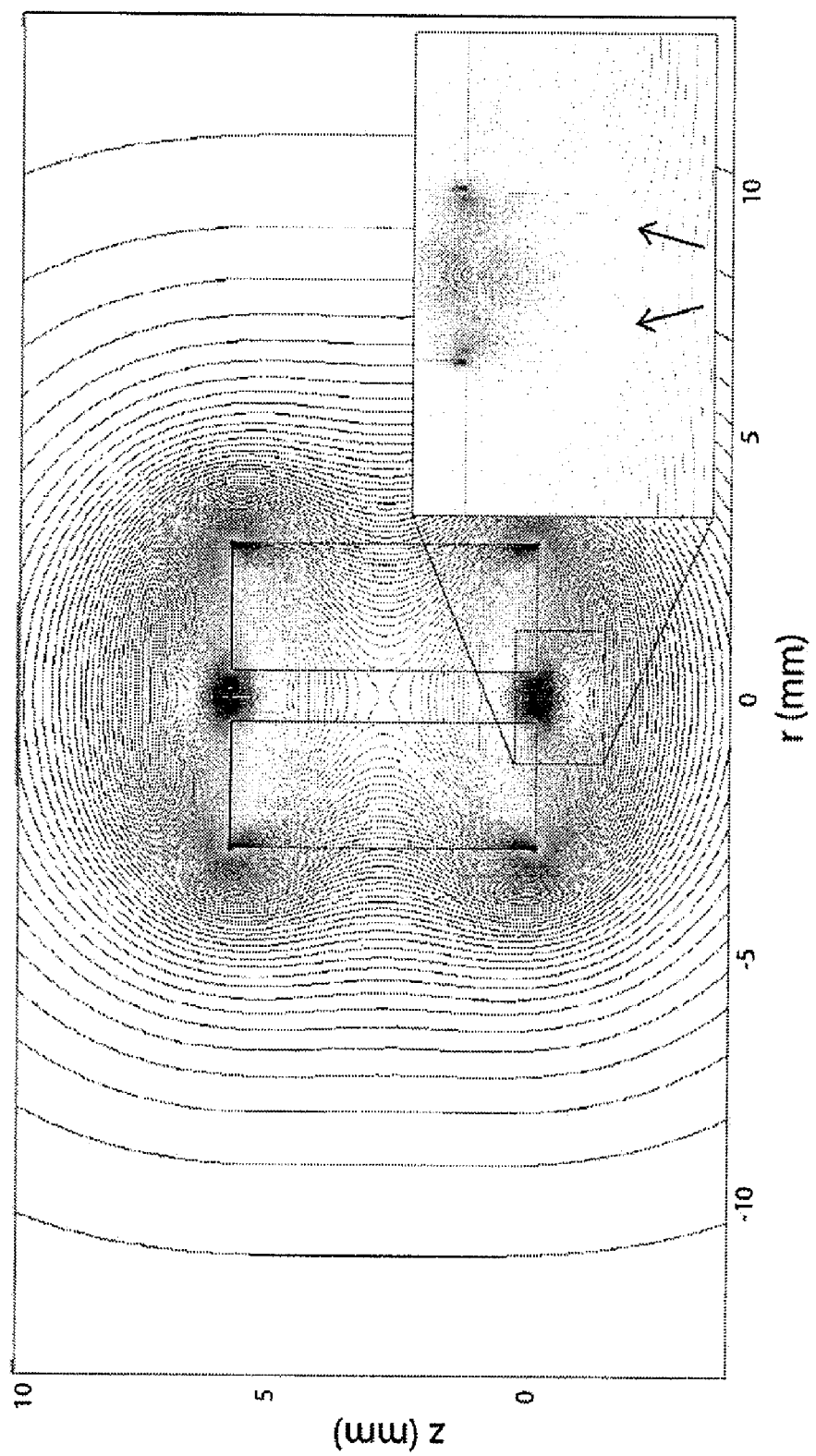
FIG. 6 presents a simulation of the magnetic field generated by the cylindrical magnet used in the experiments.

In an embodiment, we can introduce twist or turns into the molecule by rotating the probe attached to it. This can be done by using the features of the magnetic field created by the magnet 107 (for example, a cylindrical magnet) and the geometry of the magnetic probe, for example, the nanorod-bead probe shown in FIG. 1. The magnet 107 generates a vertical magnetic field $\vec{B}$. This field applies a torque $\vec{m} \times \vec{B}$ to the probe which vertically orients the probe dipole $\vec{m}$ (arrow with color gradient in FIG. 1a). The probe dipole remains aligned with the vertical field during fluctuations of the probe horizontal angle (θ in FIG. 1a) and $\vec{m} \times \vec{B} \approx 0$ at any horizontal orientation of the probe. However, fluctuations of the angle θ are constrained by a horizontal force $\vec{F}_h$ acting on the magnetic moment (or magnetic center) of the probe, due to a horizontal gradient of the magnetic field (see FIG. 6). FIG. 6 shows a simulation of the magnetic field generated by the cylindrical magnet used in the experiments (6 mm diameter, 6 mm long, with axial centered hole of 1 mm diameter and 1.2 MA/m axial magnetization) obtained using the software FEMLAB (version 3.0a). A contour plot of the magnetic flux density magnitude is shown for a cross section along the axis of the cylindrical magnet. The solution is radially symmetric around the axis r=0. The inset of FIG. 6 shows a close-up of the indicated region. Black arrows show the direction of the magnetic field gradient in the region ~2 mm away from the magnet. The horizontal (radial) component of the gradient explains the horizontal magnetic force ($\vec{F}_h$) observed in the experiments.

Figure 7:
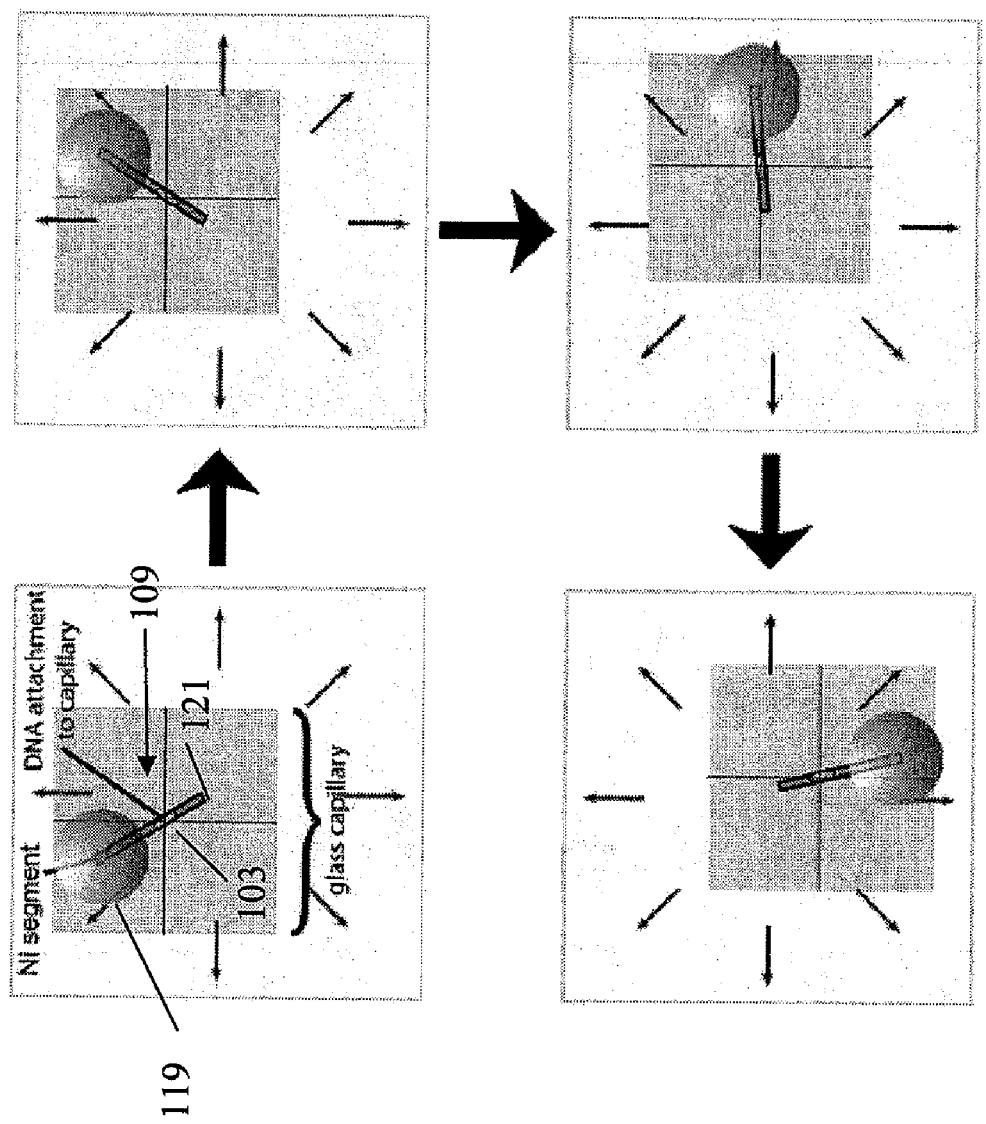
FIG. 7 presents a schematic diagram of how the magnetic probe is rotated.

The torque $\vec{L}_h \times \vec{F}_h$, where $\vec{L}_h$ is the horizontal component of the distance between the DNA point of attachment to the probe (the second binding point 115) and the magnetic moment 111 (or magnetic center) of the probe, traps the fluctuations of the angle θ 113 and orients the magnetic probe 109 (for example, the nanorod 121 of the magnetic probe 109) in the direction of the force $\vec{F}_h$ (131). That is, the second binding point 115 is offset from (does not lie on) a line extending to infinity that passes through the vector defining the magnetic moment 111. We use this alignment of the nanorod 121 with $\vec{F}_h$ (131) to rotate the magnetic probe 109. The force $\vec{F}_h$ (131) points outwards, away from the axis of symmetry of a cylindrical magnet 107 and is symmetric around this axis (FIG. 1b). $\vec{F}_h$ (131) is zero at the point where the axis of the cylindrical magnet 107 intersects the plane of the glass substrate 101 and it increases as one moves radially away from this point. For example, positioning the magnetic probe 109 at more than 50 μm from that point produces a horizontal force (131) $\vec{F}_h > 0.1$ pN. The magnetic probe 109 can be rotated by moving, for example, the sample stage in such a way that the magnetic probe 109 moves around the projected center of the cylindrical magnet 107 in a path≈50 μm away from this center (see FIG. 7). FIG. 7 shows a schematic diagram of how the nanorod-bead magnetic probe 109 is rotated. View is along the z-direction (DNA fiber axis). The horizontal force (131) $\vec{F}_h$ (0.02-0.1 pN) is generated by the gradient in field strength of the magnetic field produced by the single cylindrical magnet 107. It points radially away from the magnet center (red arrows). When the DNA attachment point does not correspond to the magnetic Ni segment, $\vec{F}_h$ (131) orients the nanorod. For example, movement of the glass substrate 101 around a square path (~100 μm side) rotates the nanorod-bead magnetic probe 109 by exposing it to a rotating horizontal force. That is, because of the radial nature of $\vec{F}_h$ (131), this motion rotates the force $\vec{F}_h$ (131) applied to the magnetic probe 109, which allows for controlled rotation of the magnetic probe 109 and thus introduces turns (or twists) into the DNA molecule 105.

Movement of the first binding point 103 relative to where the magnetic axis of the magnetic field (for example, the magnetic axis being where the horizontal force $\vec{F}_h$ is zero) intersects the substrate 101 (the magnetic axis intersection point) and/or consequent rotation of the magnetic probe 109 can be described by a winding number. For example, moving the first binding point 103 one turn counterclockwise in a closed path about the magnetic axis intersection point, while keeping the distance between the first binding point 103 and the intersection point sufficiently large so that the horizontal force $\vec{F}_h$ is great enough to rotate the magnetic probe 109 increases the winding number by one. Moving the first binding point 103 one turn clockwise in a closed path about the magnetic axis intersection point can decrease the winding number by one. The winding number can be fractional (e.g., 0.5 for one-half of a turn; 1.5 for one and one-half turns) when the angle traced by the line that joins the first binding point and the magnetic axis intersection point is not a multiple of 360 degrees.

The movement of the first binding point 103 relative to the magnetic axis intersection point to rotate the magnetic probe 109 can be achieved by holding the magnet 107 and/or the magnetic field it generates stationary and moving the first binding point 103 (for example, by moving the substrate 101). The curve traced by the first binding point 103 can be closed in some embodiments or open (for example, having the form of a spiral) in other embodiments to achieve a fractional or integer winding number of less than one, one, or greater than one. Alternatively, the movement of the first binding point 103 relative to the magnetic axis intersection point can be achieved by moving the magnet 107 and/or the magnetic field it generates and holding the first binding point 103 stationary (for example, by holding the substrate 101 stationary). The curve traced by the magnetic axis intersection point can be closed in some embodiments or open in other embodiments. Alternatively, the movement of the first binding point 103 relative to the magnetic axis intersection point can be achieved by moving the magnet 107 and/or the magnetic field it generates and moving the first binding point 103 relative to each other. The curve traced by either of the first binding point 103 and/or the magnetic axis intersection point can be closed in some embodiments or open in other embodiments.

For example, precise movement of the magnetic probe 109 can be facilitated by a manually or motor actuated stage, for example, a 2 axis motorized stage (H117 Proscan, Prior Scientific, Rockland, Mass., US). For example, the stage can be attached to the substrate 101 to move the first binding point 103. Alternatively, the stage can be attached to the magnet 107 (for example, a permanent magnet or an electromagnet) to move the magnetic axis intersection point. In the case of a cylindrical magnet 107, the magnetic axis can be approximately collinear with the geometric axis of the cylindrical magnet 107. Alternatively, other configurations can be used to move the magnetic axis intersection point and the first binding point 103 relative to each other, for example, one or more electromagnets can be used to move the magnetic field and the magnetic axis intersection point by varying electrical current delivered to the coil(s) of the electromagnet(s) without physically moving the magnet(s). After rotating to a desired configuration, the probe can be returned to the initial position with 2 pixels precision (88 nm) using a separate immobilized bead adhered to the glass surface as a reference.

Torque Measurement.

Figure 8:
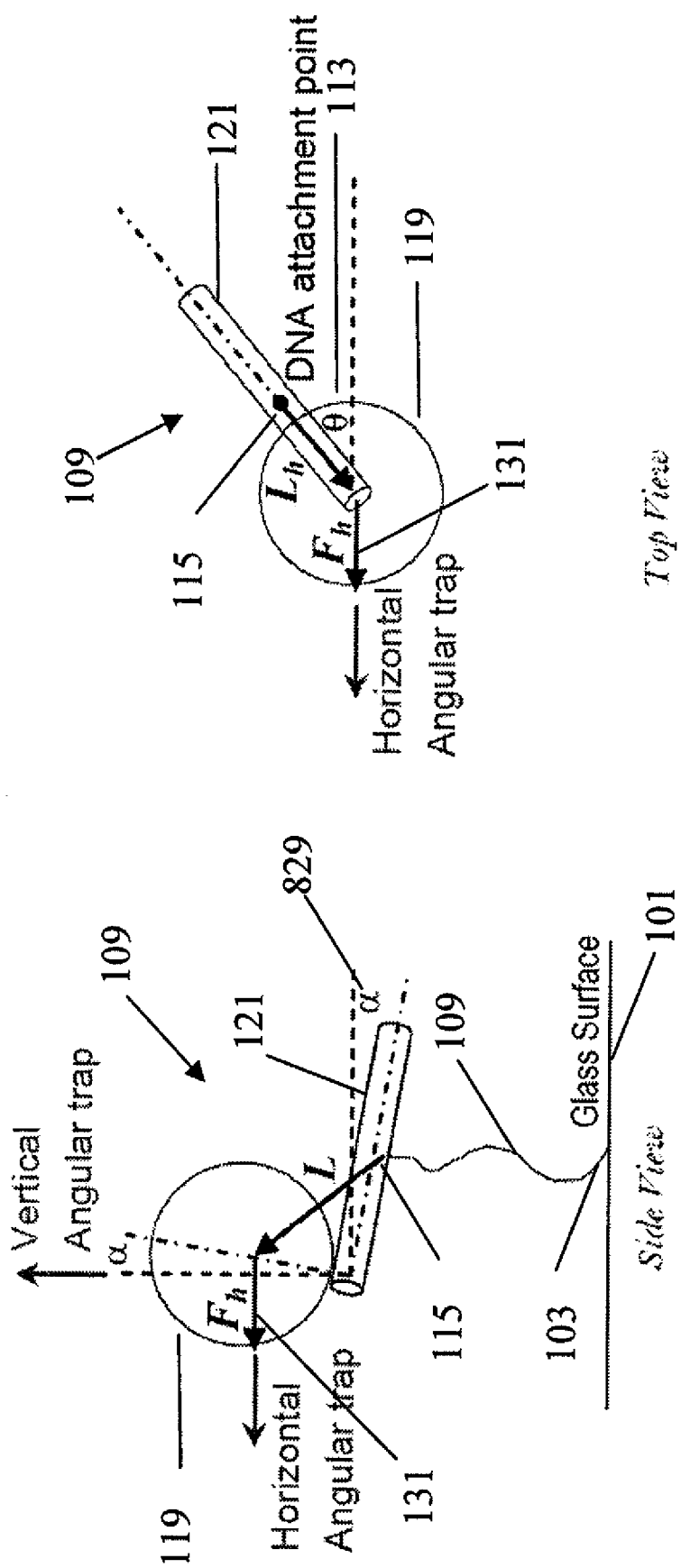
FIG. 8 presents diagrams of horizontal and vertical angular traps of the magnetic probe.
Figure 11:
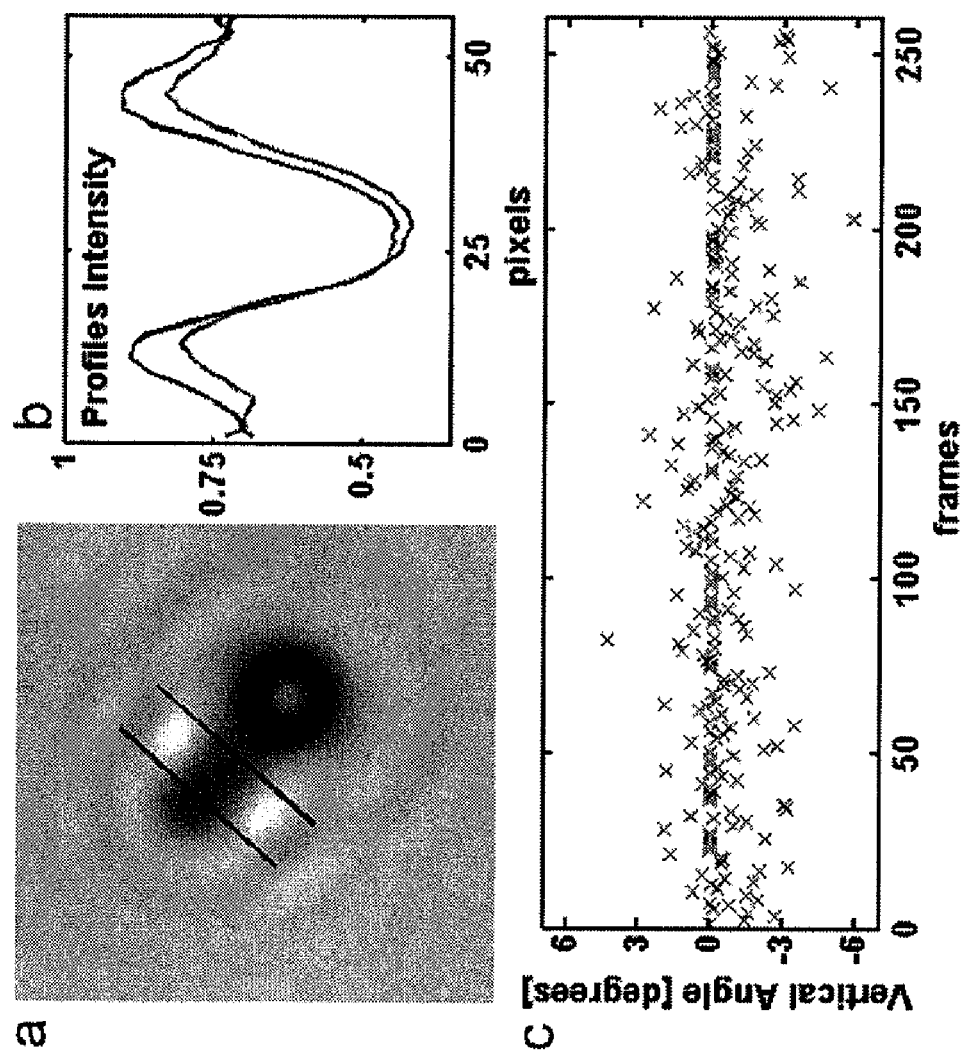
FIG. 11a-11c presents the deviation of the nanorod from the horizontal (vertical (altitude) angle).

In an embodiment, we measure torque from the horizontal (azimuthal) angular fluctuations of the magnetic probe 109 attached to the molecule 105, before and after introducing turns into the molecule 105. The probe azimuthal angle or orientation θ (113) can result from the torque of the angular trap from the magnetic field and the resistive torque from the twisted molecule 105. Measurement of molecular torque can be achieved by confinement of the magnetic probe 109 in a weak angular trap such that the change in the in angular distribution due to the resistive torque is large enough to be measured. The torque $\vec{L}_h \times \vec{F}_h$ from the magnetic field traps the fluctuations of the horizontal (azimuthal) angle of the probe (θ) (113). The angular trap stiffness ($k_\theta$) is $\approx |\vec{L}_h||\vec{F}_h|$ and therefore, is determined by the point of attachment of DNA (second binding point 115) to the magnetic probe 109 (for example, to the nanorod 121) and by the position of the magnetic probe 109 in the magnetic field (see FIG. 8). In FIG. 8 the horizontal and vertical angular traps of the nanorod-bead magnetic probe 109 are illustrated. $\vec{F}_h$ is the horizontal component 131 of the magnetic force. $\vec{L}$ is the vector from the DNA binding point (second binding point 115) to the magnetic moment 111 (or magnetic center) of the magnetic probe 109 (for example, of the magnetic bead 119). Because the magnetic bead 119 has a dipole ~15 times larger than that of the Ni segment of the nanorod (121), the magnetic moment 111 (or the magnetic center) runs approximately through the center of the magnetic bead 119. The second binding point 115 is offset from (does not lie on) a line extending to infinity that passes through the vector defining the magnetic moment 111. $\vec{L}_h$ is the horizontal component of $\vec{L}$. The nanorod-bead probe orientation can be specified by two angles (horizontal (azimuthal) angle or orientation θ (113) and vertical (altitude) angle α (829)). These angles fluctuate under the influence of two corresponding angular traps: a horizontal angular trap for θ (113) and a vertical angular trap for α (829) (arrows exterior to and pointing away from the bead 119). The horizontal angular trap is generated by $\vec{F}_h$ (131). It constrains the horizontal (azimuthal) angle θ (113) between the nanorod (121) and the direction of the force by means of a torque $\tau(\theta) = \vec{L}_h \times \vec{F}_h = F_h L_h \sin(\theta)$. Integrating and approximating $\cos(\theta) = 1 - \theta^2/2$, $E(\theta) = C + F_h L_h \theta^2/2$. The stiffness $k_\theta = F_h L_h$ is constant for a particular magnetic probe 109 at a fixed vertical pulling force (set, in the case of a permanent magnet, by the distance from the magnet 107 to the magnetic probe 109). It depends on the magnetic field at the position of the magnetic probe 109, the dipole of the probe, and the distance $L_h$. The nanorod-bead magnetic probes 109 used in an embodiment experience a horizontal angular trap of stiffness between 30 and 70 pN nm. The vertical angular trap constrains the vertical (altitude) angle α (829) by means of a torque, $\tau = C\partial(-\vec{m} \cdot \vec{B})/\partial\alpha = CmB\sin(\alpha) \approx K_\alpha \alpha$, where C is a constant that depends on the level of magnetic saturation of the magnetic probe 109. In order to characterize the vertical angular trap, we have measured the angle (α) (829) between the nanorod 121 and the horizontal plane (FIG. 11). FIG. 11 presents results of an experiment for determining the deviation of the nanorod 121 from the horizontal (vertical (altitude) angle 829). FIG. 11*a* presents a bright field image of a fluctuating nanorod-bead probe 109 tethered by a DNA molecule 105 and subject to the magnetic field created by a cylindrical magnet 107. Intensity profiles were taken from lines perpendicular to the nanorod axis. Note that the diffraction pattern remains homogeneous along the nanorod 121 which indicates that the vertical angle 829 is small. FIG. 11*b* presents intensity profiles obtained from the bright field image. The profiles shown here correspond to the last frame. FIG. 11*c* presents the vertical angle 829 as a function of movie frame. We obtained this angle from the heights of two positions and the distance between them (660 nm). The mean of the vertical angle 829 is −0.6° and its fluctuations are mostly constrained within ±3.5°. That is, in order to measure the height of two points along the axis, we first generate a calibration set of intensity profiles at each of the two positions. These calibration sets are taken at increasing objective distance while the nanorod 121 is horizontal lying on the bottom of the glass substrate 101 (same procedure is used to measure bead z-coordinate). Then we approach the cylindrical magnet 107 (i.e., move the magnet 107 closer to the magnetic probe 109) to lift the magnetic probe 109 and take intensity profiles at the two positions while the nanorod 121 is fluctuating tethered by a DNA molecule 105. The heights of the two points can be calculated by finding the best match to its intensity profile in the calibration sets.

Thus, the experiment presented in FIG. 11 demonstrates that the vertical angular trap that holds α (829) close to zero is very stiff. We calculated the stiffness of the vertical angular trap, $k_\alpha$, to be 7,213 pN·nm at low pulling force and 7,609 pN·nm at high pulling force. The nature of the vertical angular trap is such that the dipole of the probe angle is constrained by the torque $\vec{m} \times \vec{B}$ generated by steep potential energy.

Figure 9:
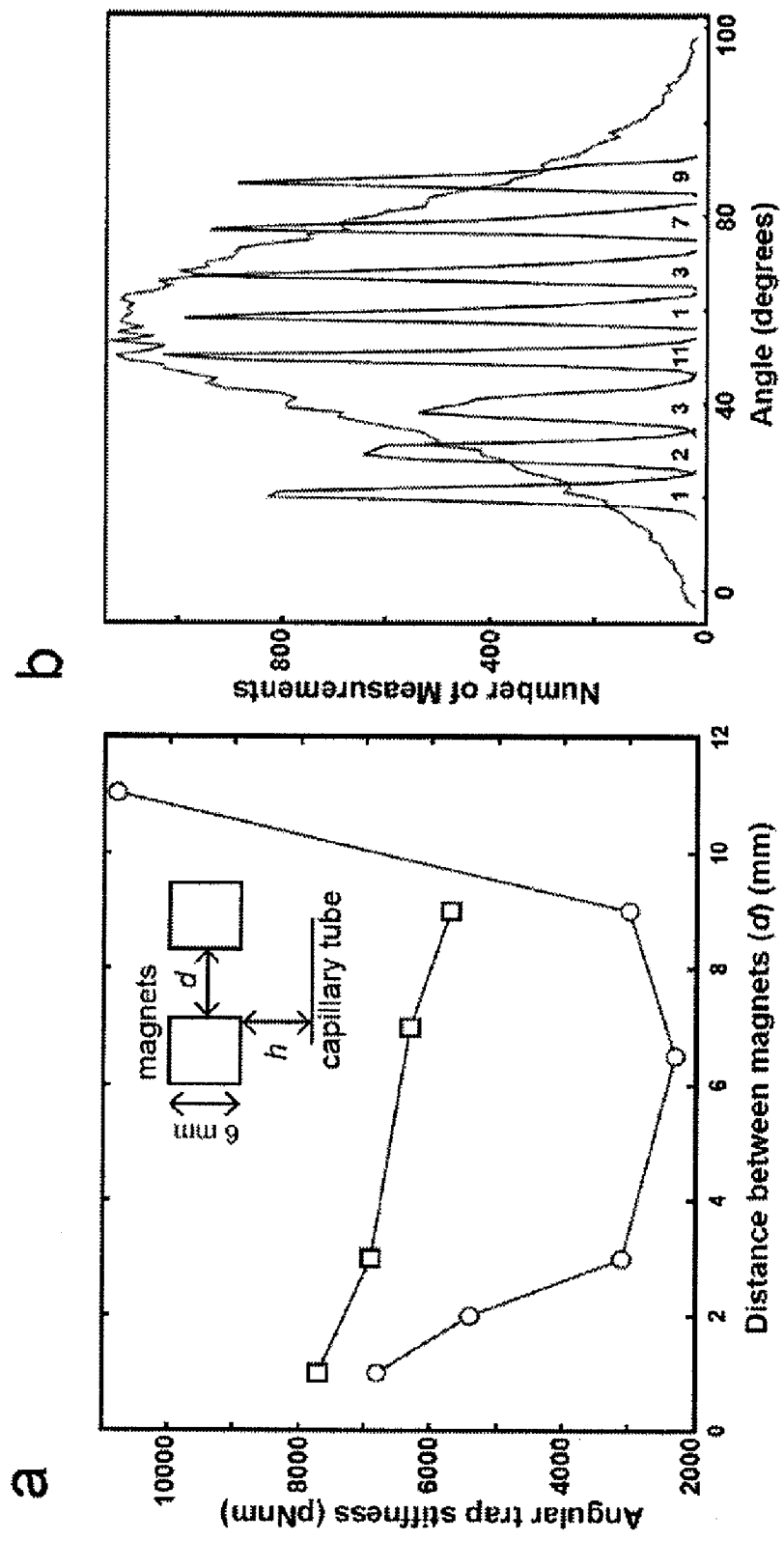
FIG. 9a presents the horizontal angular trap stiffness in the conventional two-magnet configuration.
FIG. 9b presents angle histograms.

Magnetic probes 109 can have, for example, $|\vec{L}_h|$ between 0.3 and 1 μm; and we position the magnetic probes 109 at <50 μm (for example, 40 μm) from the projected center of the cylindrical magnet 107, such that $|\vec{F}_h| < 0.1$ pN. The horizontal (azimuthal) angular trap generated by the torque $\vec{L}_h \times \vec{F}_h$ has, in these conditions, $k_\theta$ as low as 30 pN·nm. By contrast, in the conventional magnetic tweezers configuration the horizontal magnetic field generated by two magnets, tightly constrains the horizontal angular movements of the probe, producing an angular trap stiffness 80 times higher (see FIG. 9). FIG. 9*a* presents the horizontal angular trap stiffness ($k_\theta$) in the conventional two-magnet configuration as a function of distance between the magnets (d). The circle symbols show trap stiffness for a bead-bead probe using 1 μm beads. This probe self assembles in the capillary tube. The stiffness $k_\theta = k_B T / \langle \delta \theta^2 \rangle$ was measured at the minimum vertical pulling force necessary to suspend the beads above the glass surface. At each d, the vertical pulling force was set at this minimum by readjusting the distance between the magnets and the probe (h). In the two magnets setup, a shorter distance h corresponds to a greater field gradient (vertical pulling force) and a greater field magnitude experienced by the probe. The increase in $k_\theta$ at d>6.5 mm correlates with a reduction of the distance h at high values of d, required for suspending the beads off of the glass surface. The square symbols show $k_\theta$ for a nanorod probe with dipole of Ni segment along its axis. The nanorod is tethered to a DNA molecule and $k_\theta$ is measured at the minimum vertical pulling force necessary to prevent the nanorod from contacting the glass capillary. No measurements were taken at distances greater than 9 mm for the nanorod probe because the magnetic field was not able to generate a vertical force high enough to prevent the probe from contacting the glass capillary. Thus, the minimum trap stiffness of the conventional configuration is about 2,300 pN·mn. With the ability to distinguish an angle difference of 1°, torques less than 2,300·2π/360, or ~40 pN·mn, are not detectable. In FIG. 9*b* angle histograms for some of the experiments described in FIG. 9*a* are shown. Each histogram represents 3,000 angle measurements, bin size 1°. The leftmost four steep peaks are histograms from bead-bead probes and the rightmost four steep peaks are from nanorod probes. Distance between magnets (d) in millimeters is indicated under each curve. Angular distribution of a nanorod-bead probe under the magnetic field created by a cylindrical magnet 107 according to the present invention is shown for comparison (broad curve). The angular trap stiffness generated by the cylindrical magnet 107 was 33 pN·mn, about 80 times lower than the lowest value of the two-magnets configuration. Therefore, conventional magnetic tweezers have a resolution of not better than 40 pN·nm and cannot be used to measure torque. The low trap stiffness in our configuration allows a torque resolution of <1 pN·nm, essential for torque measurements on DNA, which at a pulling force of 1 pN, buckles at 17 pN·nm.[9]

To obtain the configuration shown in FIG. 1*a*, the axis of the nanorod 121 can be approximately horizontal under the vertical magnetic field. The precision of torque measurement using this configuration can be enhanced if the angular fluctuations of the rod out of the horizontal plane (vertical (altitude) angular fluctuations) are minimized. Minimizing these fluctuations ensures that the horizontal distance $\vec{L}_h$ is constant, which conserves the torque $\vec{L}_h \times \vec{F}_h$, and also conserves the shape of the nanorod image, which allows tracking the angle of the nanorod 121 with precision (see FIG. 2). This particular configuration of the nanorod is accomplished by limiting the length of the ferromagnetic Ni segment 1001 of the nanorod 121 to ~0.1 μm, approximately half of the nanorod diameter, which makes the magnetic dipole of the Ni segment perpendicular to the long axis of the nanorod[25] (see FIG. 10). The short Ni segment 1001 and the longer Pt segment 1003 of the nanorod 121 can be seen in FIG. 10*b*.

The magnetic attraction between the ferromagnetic Ni segment 1001 and the magnetic dipole that it induces in a superparamagnetic bead 119 results in self-assembly, as illustrated in FIG. 1*a*. In the assembled probe 109, the Ni segment 1001 attaches the nanorod 121 to the bead 119 in such a way that under a vertical magnetic field, the dipole of the bead and the dipole of the Ni segment can be approximately vertical while the nanorod axis can be approximately horizontal. Vertical (altitude) angular fluctuations 829 of the nanorod 121 are strongly constrained by this alignment of the probe dipole with the vertical magnetic field. Measurements of the angle between the nanorod 121 and the horizontal plane show that the vertical (altitude) angle 829 fluctuates within ±6° (see FIG. 11).

Figure 12:
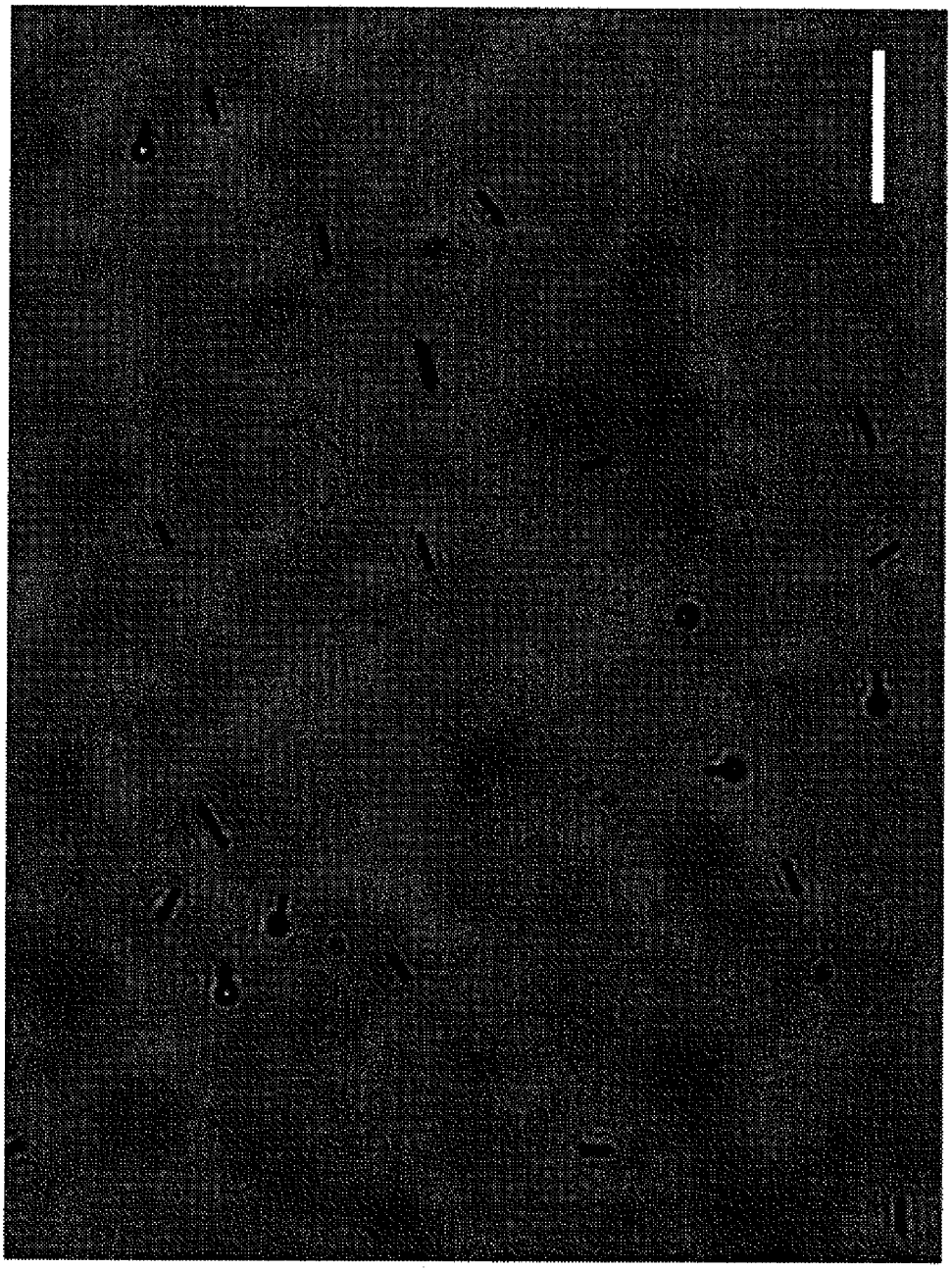
FIG. 12 presents a bright field view of nanorod-bead magnetic probes (bar=5 µm).

In contrast to a random attachment of a nonmagnetic particle to a magnetic bead, the attachment driven by the ferromagnetic Ni segment 1001 of the nanorod 121 produces a uniform population of magnetic probes 109 with the desired configuration (see FIG. 12). FIG. 12 presents a bright field view of nanorod-bead magnetic probes 109 (bar=5 μm). Ni—Pt nanorods 121 and superparamagnetic beads 119 self assemble after mixing in the capillary tube by magnetic attraction between both particles, without the action of an external magnetic field. In this image, individual nanorods 121 and magnetic beads 119 are also seen, which adhere nonspecifically to the glass substrate 101 and do not interfere with measurements.

FIG. 2a presents a bright-field image of a nanorod-bead magnetic probe 109 (bar=1 μm). The probe is tethered to a glass substrate 101 by a DNA molecule 105 and pulled with a vertical magnetic field. The asymmetry of the magnetic probe 109 allows for precise angular measurement by an imaging device 117. FIG. 2b presents a binary image of a nanorod-bead magnetic probe 109. The dashed line is the computed orientation of the magnetic probe 109 based on the center of the bead 119 and the center of the rod 121.

Figure 3:
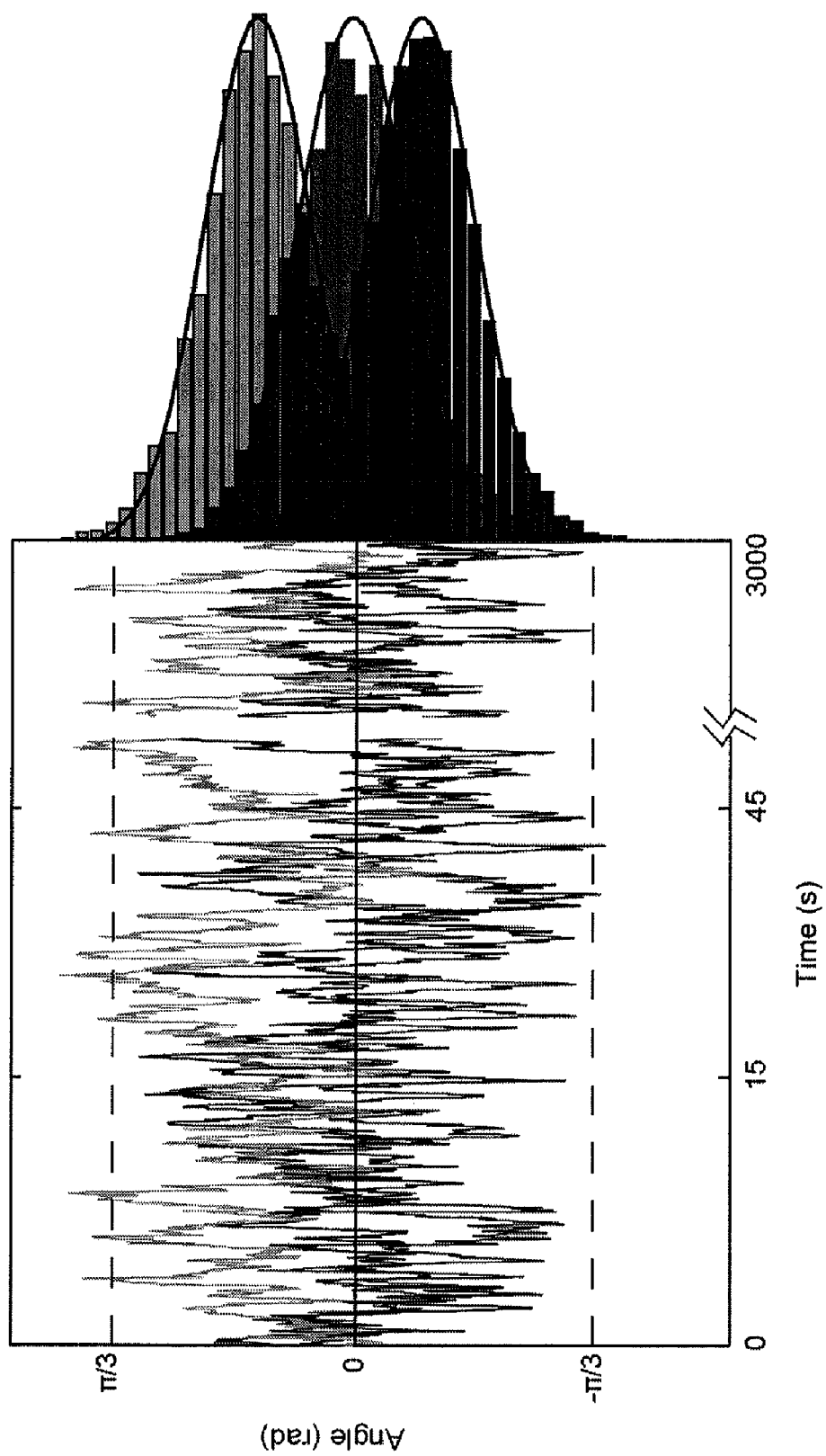
FIG. 3 presents measurements of the horizontal (azimuthal) angle (θ) of a nanorod-bead magnetic probe tethered to a DNA molecule with different numbers of turns as a function of time and as histograms. The lower histogram, the middle histogram, and the upper histogram are derived from consecutive angle measurements at −40, 0, +45 turns respectively.

FIG. 3 shows measurements of the horizontal (azimuthal) angular (θ) fluctuations of a nanorod-bead magnetic probe 109 tethered to a DNA molecule 105 for different numbers of turns. The time series data are used to generate histograms. The lower histogram, the middle histogram, and the upper histogram are derived from consecutive angle measurements at −40, 0, −+45 turns respectively.

The torque at n number of turns can be obtained from two angular histograms, because angular fluctuations of the nanorod-bead magnetic probe 109 attached to a filament 105 or fiber report on the torque experienced by the magnetic probe 109. The net potential energy of the magnetic probe 109 is a combination of the forces from the imposed magnetic field and the elasticity of the molecule as a function of the probe azimuthal angle 113:

$$U = U_B(\theta) + E(\theta)$$

where $U_B(\theta)$ is the potential energy of the magnetic probe 109 in the magnetic field. E is the elastic energy of the molecule 105 as a function of the attached probe angle. Note that $U_B(\theta)$ is a periodic function of θ (period=2π), but E is not. The angular fluctuation of the probe is given by the Boltzmann distribution $$P(\theta) \propto e^{-U/k_BT}$$

To obtain torque at n turns of the molecule (θ=2πn), the angular histogram $P_0(\theta)$ of the nanorod-bead magnetic probe 109 is first obtained before introducing turns into the molecule (n=0). $P_0(\theta)$ describes the angular probability distribution of the magnetic probe 109 in the absence of resistive torque from the molecule 105. We fix the θ axis such that $\langle\theta\rangle = 0$ in the $P_0(\theta)$ distribution. Then, by moving the stage, we introduce n turns into the molecule 105 (see FIG. 7) and collect a new angular distribution, $P_n(\theta)$, at the same (x,y) position in the field as $P_0(\theta)$. The most probable angle, θ*, of this new distribution corresponds to a minimum of the net potential energy U, thus:

$$\frac{d(U_B(\theta))}{d\theta}\bigg|_{\theta=\theta^*} + \frac{d(E_n(\theta))}{d\theta}\bigg|_{\theta=\theta^*} = 0$$

where $E_n(\theta)$ is the elastic energy in the vicinity of 2πn. The second term of this expression is the resistive torque applied by the molecule 105 to the magnetic probe 109 at n turns (−$\tau_n$).

The resistive torque of the molecule 105 can be estimated by approximating the angular trap of the field as a harmonic potential well. Approximating the magnetic contribution by a quadratic function (harmonic approximation) $U_0 + k_\theta \theta^2/2$, we have $\langle\theta\rangle = \theta^*$, we obtain, $$\tau_n = k_\theta \langle\theta\rangle$$

$k_\theta$ is calculated from the mean square deviation of θ distribution, $k_BT/\langle\delta\theta^2\rangle$. Thus, the trap stiffness $k_\theta$ multiplied by the change in the average angle between $P_n(\theta)$ and $P_0(\theta)$ gives the torque at n turns. Trap stiffness ($k_\theta = k_BT/\langle\delta\theta^2\rangle$) is 34.5, 35.5 and 35.1 pN·nm at 0, −40, +45 turns respectively. The angle measurements shown in FIG. 3 are used to obtain the torque values (−10.4 and 13.7 pN·nm) of the curve at pulling force 0.6 pN shown in FIG. 4.

Torque can also be obtained from $P_n(\theta)$ and $P_0(\theta)$ without approximating the magnetic angular trap as a harmonic potential. The ratio of angular distributions is $$\frac{P_n(\theta)}{P_0(\theta)} \propto e^{-(E_n(\theta)-E_0(\theta))/k_BT}$$

The contribution of the magnetic field has been canceled out. At low pulling forces and n=0, $E_0(\theta)$ is essentially a constant function and the molecular torque is zero. Thus, the elastic free energy of the molecule can be obtained from the log of the distributions ratio:

$$E_n(\theta) = -k_BT \ln \frac{P_n(\theta)}{P_n(\theta)} + Const.$$

The molecular torque at n turns is the slope of the free energy, or $$\tau_n = \frac{\partial E_n}{\partial \theta}.$$

$\tau_n$ can be obtained by fitting a straight line to the log of the distributions ratio. The difference between torque values obtained with and without the harmonic approximation is less than 1.5 pN·nm and typically less than 0.5 pN·nm (data not shown).

Torque measurements can be made with the angular trap from the magnetic field not changing after turns are introduced into the molecule. We test this by calculating $k_\theta$ at different number of turns. No significant change in $k_\theta$ is observed associated with the change in $\langle\theta\rangle$ or with the change in the z position of the magnetic probe 109 (FIG. 3 and Table 1).

TABLE 1

Figure 4:
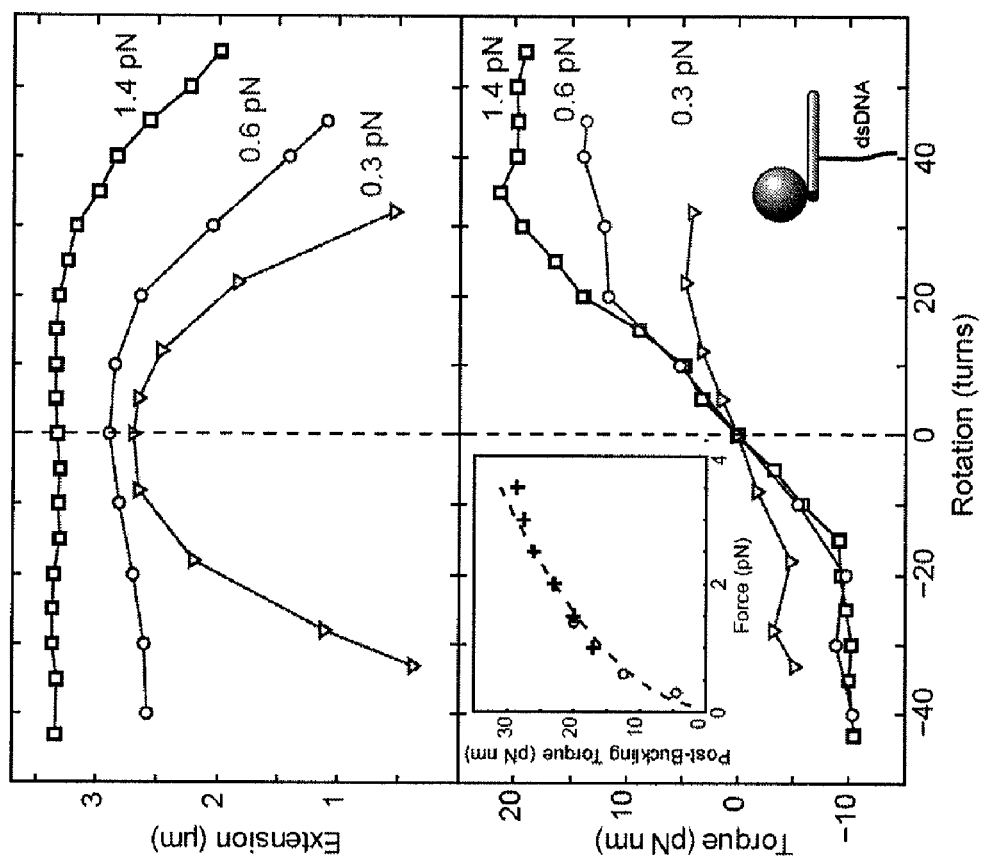
FIG. 4 presents results of single-molecule torque measurement of DNA at low pulling force. Results of extension (elongation) and torque measurement of a 10 kb naked DNA molecule at pulling forces of 0.3, 0.6 and 1.4 pN are shown. Inset: The torque at which DNA buckles to form plectonemes at positive rotations (post-buckling torque) as a function of pulling force. Black crosses are Forth et al. measurements[9] and the dashed line represents a theoretical model proposed by Marko.[26] Circles are the post-buckling torques from curves at 0.3, 0.6 and 1.4 pN.

Angular trap stiffness ($k_\theta$) and changes in equilibrium angle
$\langle\theta\rangle$ for curve at 0.6 pN in FIG. 4.

| Turns | Molecule extension (μm) | Number of angle measurements | $k_\theta$* (pN·nm) | $\langle\theta\rangle$ (°) | $\langle\theta\rangle$ (rad) | Torque** (pN·nm) |
|---|---|---|---|---|---|---|
| 0 | 2.9 | 18,000*** | 34.5 | 0 | 0 | 0 |
| −40 | 2.58 | 6,000 | 35.5 | −17.27 | −0.301 | −10.4 |
| −30 | 2.61 | 6,000 | 32.8 | −14.61 | −0.255 | −8.8 |
| −20 | 2.7 | 6,000 | 31.6 | −16.44 | −0.287 | −9.9 |
| −10 | 2.81 | 6,000 | 33 | −8.96 | −0.157 | −5.4 |
| 10 | 2.85 | 6,000 | 34.6 | 8.63 | 0.151 | 5.2 |
| 20 | 2.64 | 6,000 | 34.8 | 19.26 | 0.336 | 11.6 |
| 30 | 2.04 | 6,000 | 33.2 | 19.92 | 0.348 | 12 |
| 40 | 1.41 | 6,000 | 37.2 | 23.08 | 0.402 | 13.9 |
| 45 | 1.09 | 6.000 | 35.1 | 22.75 | 0.397 | 13.7 |

*$\langle k_\theta \rangle$ = 34.23 pN · nm, $\sigma_{k\theta}$ = 1.61 pN · nm. To estimate the variation in $k_\theta$ of histograms at constant number of turns, $k_\theta$ is calculated from the 3 sets of 6,000 measurements at zero turns, giving σ = 1.45 pN · nm, which indicates that most of the variation observed in trap stiffness originates in drift during angle measurements and not in systematic errors associated with $\langle\theta\rangle$ or with probe z position.

**Torque was calculated using the stiffness kg at zero turns. τ = $k_\theta$(0) · $\langle\theta\rangle$
***More angle measurements were taken at zero turns to obtain a precise value of $k_\theta$(0).

Figure 13:
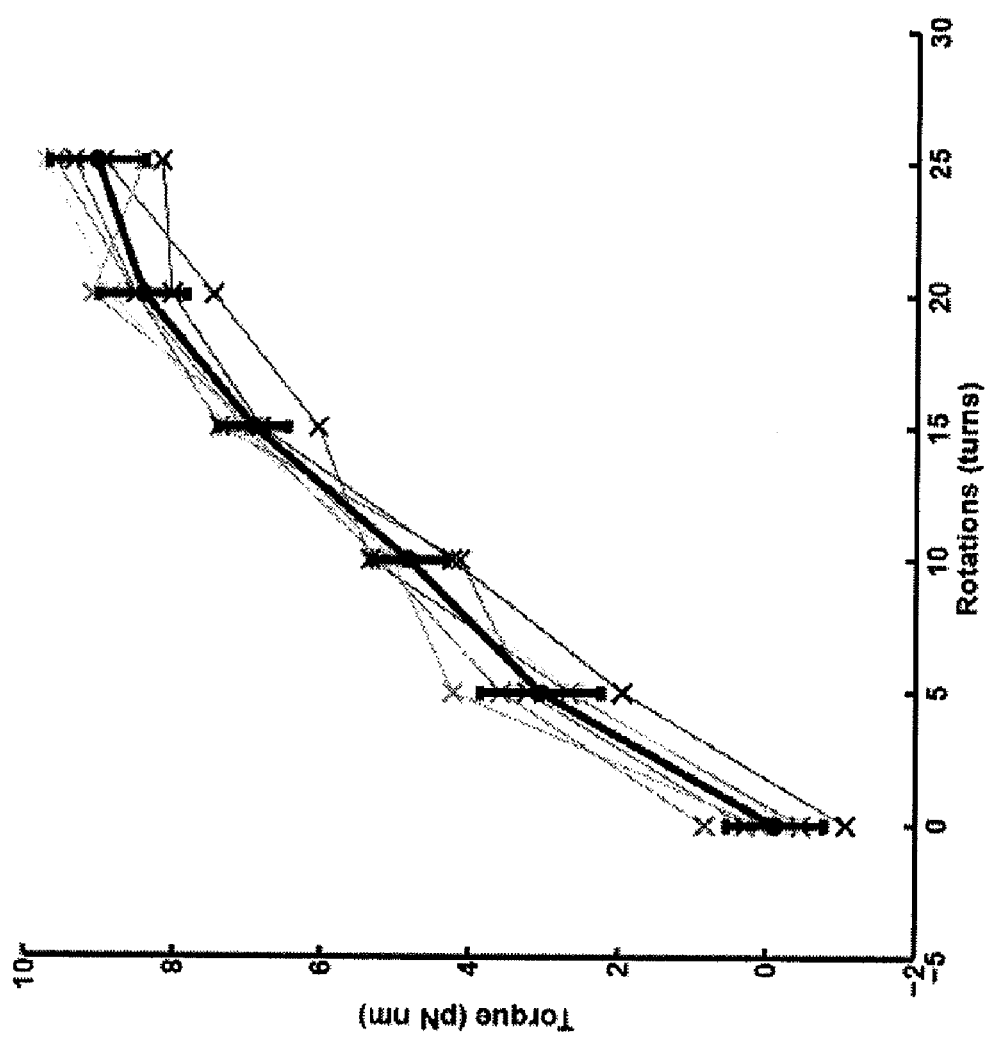
FIG. 13 presents an assessment of the precision of the torque measurements.

The observed stability of $k_\theta$ is a consequence of the horizontal force being constant for z changes in the scale of the experiment and the nanorod 121 being highly constrained to the horizontal plane. Multiple torque measurements in two different DNA molecules 105 give a standard deviation of 0.8 pN·nm or less (see FIG. 13). FIG. 13 presents an assessment of the precision of the torque measurements. Torque was obtained for two DNA tethered probes at a vertical pulling force of 0.4 pN (3 curves from each molecule). The standard deviation of torque values (N=6) was always below 0.8 pN·nm. Torque measurements are affected by slow drifts in the system. Two sources of variability in our measurements were stage and magnet drift. In order to minimize the stage drift we used a reference bead adhered to the bottom of the capillary tube. Before obtaining each histogram, the position of the stage was corrected using the image of an immobilized bead. This provided a positional precision of 2 pixels (88 nm) in each direction.

The torque required to change the orientation of the magnetic probe 109 by the minimum detectable angle gives the torque resolution of the instrument. The nanorods 121 allow detection of ~1° change. The horizontal angular trap imposed on the nanorod-bead magnetic probe 109 by the cylindrical magnet 107 can be approximated to the harmonic potential (See FIG. S3):

$$U_B(\theta) = C + \frac{1}{2}F_h L_h \theta^2 = C + \frac{1}{2}k_\theta \theta^2$$

The torque τ required to displace the minimum of the potential energy by an angle θ* is $k_\theta \theta^*$. We use magnetic probes 109 with trap stiffness ($k_\theta$) between 30 and 70 pN·nm and we can detect ~2π/360 radians change. Thus, an embodiment of a system or instrument according to the present invention has a theoretical torque resolution of $k_\theta$ (2π/360) (between 0.5 and 1.2 pN·nm). The potential that traps the horizontal angular fluctuations in conventional magnetic tweezers, where magnetic field and probe dipole are horizontal, is:

$$E(\theta) = -C\vec{m}\cdot\vec{B} \approx -CmB\left(1 - \frac{1}{2}\theta^2\right) = -CmB + \frac{1}{2}k_\theta \theta^2$$

where C is a constant that depends on the level of magnetic saturation of the probe. In this case, $k_\theta$=CmB. This angular trap is significantly stiffer than the one generated by the system composed by cylindrical magnet 107 and nanorod-bead magnetic probe 109. The minimum $k_\theta$ that we find for the conventional magnetic tweezers configurations that we tested was 2,300 pN·nm (FIG. S4). With this stiffness the instrument has resolution of 2,300 pN·nm (2π/360)=40 pN·nm.

Molecule Extension.

Molecule (or filament) extension can be measured from the interference pattern of the bead.[24] This method allows us to measure molecule extension with <50 nm precision. The z-coordinate of the center of the bead 119 of the nanorod-bead magnetic probe 109 can be obtained by finding the best match of the bead interference profile in a calibration profile set. The profile set can be obtained at increasing distances from the objective with 50 nm steps using the motorized z-stage.[27] Stage drift can be corrected by parallel tracking of the z-coordinate of a separate bead stuck to the bottom of the capillary tube.

Figure 2:
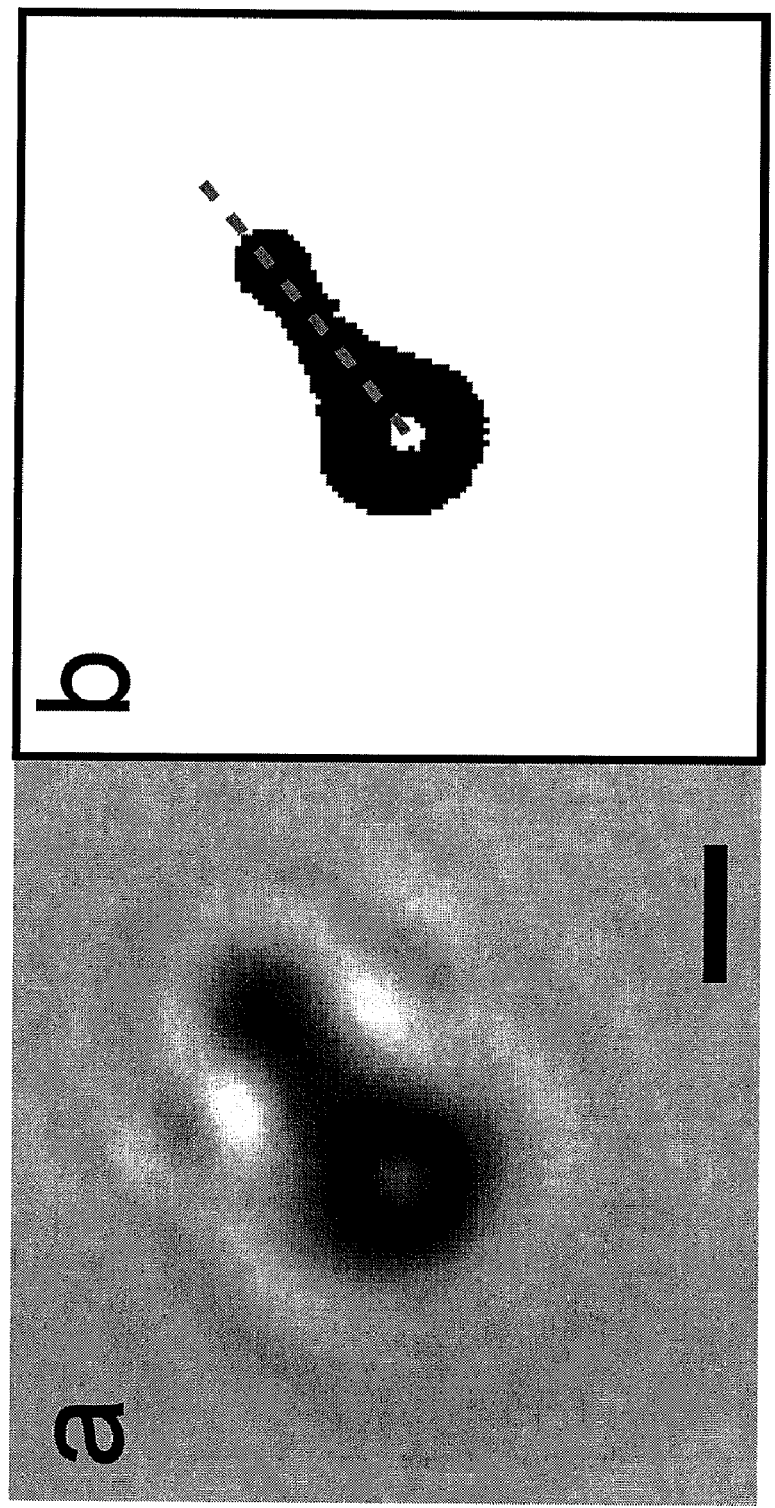
FIG. 2a presents a bright-field image of a nanorod-bead magnetic probe (bar=1 µm).
FIG. 2b presents a binary image of a nanorod-bead magnetic probe.

We can calculate vertical pulling force in each of our torque measurements from the x and y fluctuation of the DNA point of attachment to the magnetic probe 109 (second binding point 115).[2] Each degree of freedom of the magnetic probe has an average energy $k_B T$ which allows us to obtain the force as $$F = \frac{k_B T l}{\langle \delta x^2 \rangle}$$

where l is the vertical distance between the attachment point (first binding point 103) of the molecule 105 to the glass substrate 101 and the attachment point (second binding point 115) of the molecule 105 to the probe 109 (z-coordinate of the center of the bead 119). In our case, x is the coordinate of the DNA point of attachment (second binding point 115) at the nanorod 121. Since the nanorods 121 are fully covered with Neutravidin we do not know this position, but we can calculate it from the fluctuations of the probe. The DNA binding point is the center of rotation of the object. This point does not rotate, so it is the point along the axis of the probe that minimizes $\langle \delta x^2 \rangle$. It is in the range 0.3-1 μm away from the magnetic section of the nanorod 121 (which coincides with the center of the bead 119 in the image) in the magnetic probes 109 we use. FIG. 2 shows the axis of the nanorod 121 (line) along which we find the center of rotation.

The system cylindrical magnet 107 and nanorod-bead magnetic probe 109 can apply forces between 0.1 pN and 1.5 pN using 1 μm diameter beads 119. Larger beads (2.8 μm) are expected to generate vertical pulling forces of up to 10 pN.

Pulling (Elongational) Force.

The vertical gradient of the magnetic field produces a vertical pulling force. For example, changing the distance between the cylindrical magnet 107 and the glass substrate 101 in a 1 mm range allows adjustment of this force between about 0.1 and about 1.5 pN. The magnetic probes 109 are tethered to DNA or chromatin 105, and the vertical pulling force is computed from the fluctuations of the x-y position of the point along the nanorod where the DNA is attached.[13]

Probe Assembly.

The experiment is performed inside a capillary tube 123 over an inverted microscope 125 as shown in FIG. 1c. One end of a linear DNA fragment (10 kb) can be functionalized with several digoxigenin moieties and the other end with several biotin moieties. The same DNA fragment is used for chromatin reconstitution and naked DNA experiments. Functionalized DNA or chromatin (50 ng/ml) is incubated for 10 min in an anti-digoxigenin coated capillary tube 123. Nanorods 121 are functionalized by coating nonspecifically with neutravidin during a 30 min incubation (see FIG. 14), mixed with the superparamagnetic beads 119, and introduced into a capillary 123 containing functionalized DNA or chromatin. Nanorods 121 and beads 119 self assemble and sediment on the bottom of the glass capillary 123, and are lifted by placing the capillary tube 123 under the cylindrical magnet 107. In the resulting constructs, DNA or chromatin fibers are torsionally constrained because they are attached to the nanorod 121 through multiple biotin/neutravidin linkages, and to the glass substrate 101 through multiple digoxigenin/anti-digoxigenin linkages.

Measurements.

We use the nanorod-bead magnetic probes 109 and the cylindrical magnet 107 configuration to track the motions of single 10 kb DNA molecules 105. The nanorod-bead magnetic probes 109 allow simultaneous tracking of horizontal angular fluctuations (torque), molecule extension, and pulling force. Results of single-molecule torque measurement of DNA at low pulling force are shown in FIG. 4. Results of extension and torque measurement of a 10 kb naked DNA molecule at pulling forces of 0.3, 0.6 and 1.4 pN are shown. Extension and torque are symmetric for 0.3 pN and asymmetric for 0.6 and 1.4 pN. Introduction of sufficient positive rotations (overwinding DNA) generated plectonemes, indicated by linear shortening and constant torque. Negative rotations (unwinding DNA) at 0.6 and 1.4 pN pulling forces failed to shorten the DNA due to DNA melting, and resulted in a constant torque of ~−10 pN·nm. Negative twisting at the lower pulling lower force of 0.3 pN allowed DNA shortening, indicative of negative plectoneme formation with a torque of 4-5 pN·nm. The inset of FIG. 4 presents the torque at which DNA buckles to form plectonemes at positive rotations (post-buckling torque) as a function of pulling force. Black crosses are Forth et al. measurements[9] and the dashed line represents a theoretical model proposed by Marko.[26] Circles are the post-buckling torques from curves at 0.3, 0.6 and 1.4 pN. Our measurements match previous measurement at ~1 pN and agree with the theoretical prediction at low pulling forces (<1 pN). The parameters used in the model (dashed line) are 50, 100 and 28 nm for the bend persistent length, twist persistent length, and twist stiffness of the plectonemic state.

Our measurements for DNA extension and resistive torque as a function of turns agree with and extend previously published observations.[9,11,12] Positive rotations (to overwind DNA) and negative rotations (to unwind DNA) are introduced into the DNA at pulling forces between 0.3-1.4 pN. For pulling forces of 0.6 and 1.4 pN, the torque is a linear function for low number of rotations. The linear behavior is interrupted at ≈−20 turns, corresponding to a ratio between the turns introduced in the molecule 105 and the molecule intrinsic number of helix turns of ≈−0.02. As more negative turns are introduced, melting of the duplex DNA occurs,[13] and the torque is constant at −10 pN·nm. A similar value (−9.6 pN·nm) was obtained by Bryant et al. at pulling forces of 15 pN and 45 pN.[12] At 0.3 pN and higher pulling forces, the linear behavior of the torque curve is also interrupted at positive turns. The exact number of rotations at which this happened is force-dependent and coincides with the buckling transition where plectonemic DNA started to form. The torque remains flat after DNA buckling (post-buckling torque), which has been observed at pulling forces above 1 pN,[9,10,12] and is consistent with a phase transition between extended and plectonemic DNA.[26] The inset in FIG. 4 shows the post-buckling torque in our measurements (circles), the values obtained in previous measurements at forces above 1 pN [ref.[9]] (black crosses), and a theoretical prediction of DNA post-buckling torque[26] (dashed line). The post-buckling torque in our measurements matches previous experimental results at ~1 pN and agrees with the theoretical curve in the low pulling force regime (<1 pN), where previous experimental measurements are not available.

Figure 5:
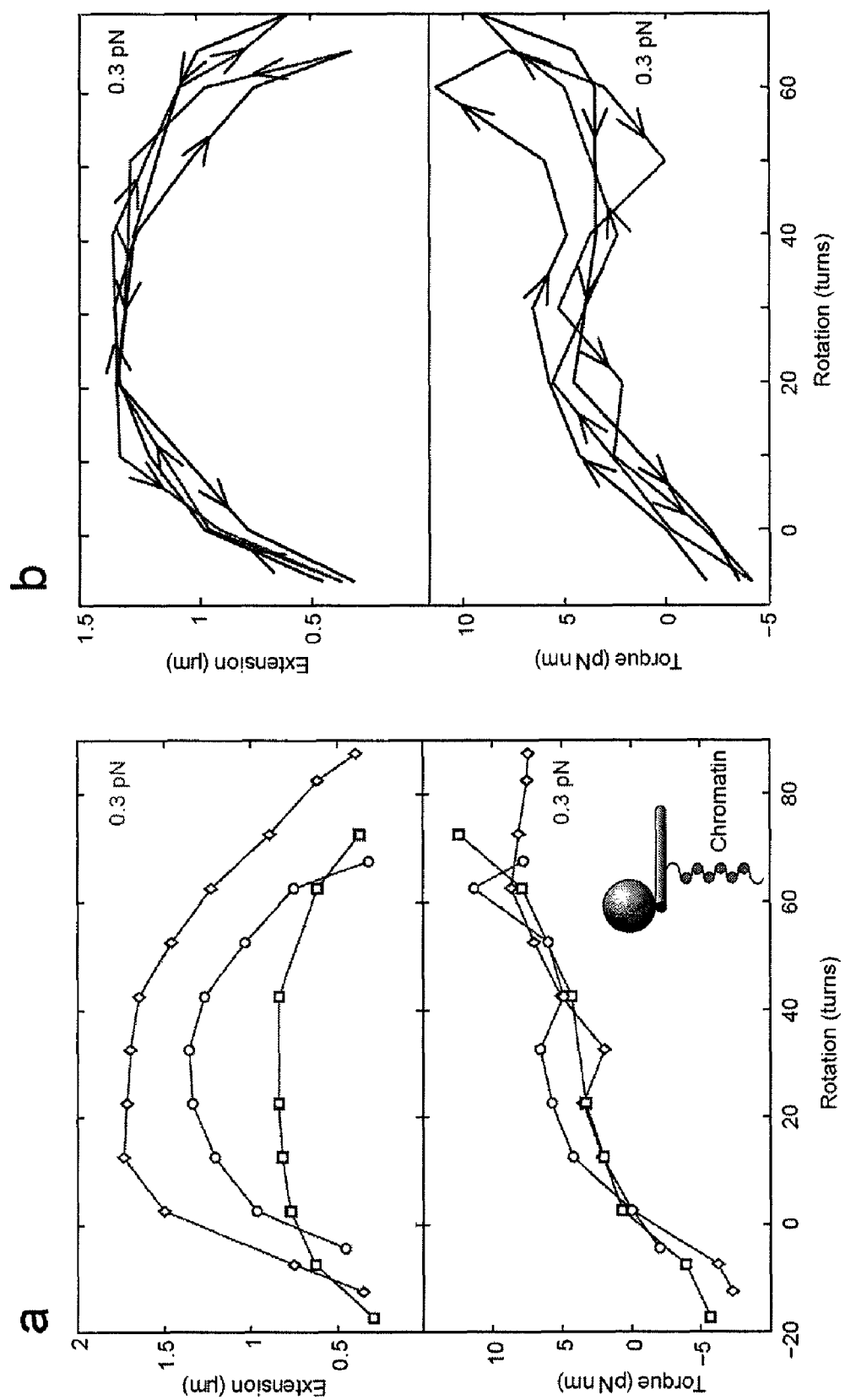
FIG. 5 presents results of extension and torque measurements on chromatin fibers.

The resistive torque of chromatin fibers 105 has not been experimentally measured previously. We obtain turn-vs-extension and turn-vs-torque curves for chromatin at 0.3 pN vertical pulling force, which is sufficiently low to prevent DNA melting when it is twisted. FIG. 5 presents results for extension and torque measurements of chromatin fibers 105. Chromatin was generated from the same DNA used for bare DNA experiments described in FIG. 4. The chromatin fibers 105 are reconstituted using recombinant *Xenopus* histones and the same 10 kb DNA fragment as for the bare DNA experiments. The experiment is performed at low ionic conditions (10 mM phosphate buffer).

The turn-vs-extension and turn-vs-torque curves at 0.3 pN pulling force are shown for three molecules 105 in FIG. 5a. The extension curves are significantly flatter than for the naked DNA at the same vertical pulling force (0.3 pN). They were also highly variable from molecule to molecule, which has been previously observed and correlated with the number of nucleosomes per fiber.[2] Bancaud et al.[8] obtained the relation between the topological shift and the maximal extension of nucleosome arrays (FIG. 5a in their paper). The slope of the observed linear trend was −12 turns/0.7 μm=−17.1 turns/μm. Bancaud et al. also estimated the topological change of one nucleosome to equal −0.8 turns. So, the number of nucleosome particles per micrometer is 17.1/0.8=21.4. In our measurements, the length difference between the maximal extensions of the shortest (0.8 μm long) and longest (1.7 μm) fibers 105 in FIG. 5a is 0.9 μm which corresponds to a difference of 19.3 nucleosomes. In spite of this, each molecule is able to accommodate >+40 turns and the torque remains below 7 pN·nm before significant shortening occurs (FIG. 5a). This contrasts with naked DNA, which at the same pulling force, can only accommodate ~20 turns before shortening over a change in torque of 7 pN·nm (FIG. 4). This shows that extended chromatin fibers 105 have a significantly lower torsional rigidity than bare DNA.

Chromatin fibers 105 have previously been reported to display hysteresis in single molecule twist-extension experiments.16 We find that such a twist-extension hysteresis is also coupled with torque hysteresis. That is, FIG. 5b shows that extension and torque hysteresis was observed in the chromatin fibers 105. Two consecutive loops are shown for a single molecule. Hysteresis is observed at >+50 turns: Backward (to the left) paths show larger extension and lower torque. Hysteresis presumably indicates the formation of torsionally-induced structural states that do not relax on the timescale of the experiments.

In summary, embodiments of the system and methods according to the present invention enable the measurement of torque on single biomolecules. A nanorod-bead magnetic probe 109 manipulated with a vertical magnetic field is a component for measuring resistive torque with pN·nm resolution. In parallel with torque, molecule extension and pulling forces can be precisely measured. For the first time, torque at a physiologically relevant low pulling force (<1 pN) has been measured in a single molecule experiment. Our method is simple, and does not require extensive calibration or feedback systems. The use of magnetic probes 109 produced by self assembled magnetic nanorods 121 and superparamagnetic beads 119 creates new possibilities for magnetic manipulation of single molecules 105.

The method for determining the torque on a filament 105 has been implemented in software. The software was written in Matlab using the image analysis, image acquisition, and signal analysis toolbox. The software allows for measuring the torque applied to the filament 105 from the difference in the angular distribution of the magnetic probe 109 attached to the filament 105 before and after turns are introduced in the filament. The software tracks the position of two objects in two independent video streams coming from the same video (e.g., CCD) camera 127: a magnetic probe 109 attached to the filament 105 and a reference bead attached to the bottom of a (e.g., glass) substrate 101. The position (x, y, z) of the magnetic probe 109 is corrected with the position (x, y, z) of the reference bead to account for drifts in the system. The (azimuthal) angle of the magnetic probe 109 is tracked at 21 Hz. Torque measurement can be made, for example, by obtaining angular distributions of about 6000 measurements, which can be obtained, for example, over about 5 minutes. The software can determine torque on the filament 105, extension of the filament, and applied vertical (elongational or pulling) force.

Software can be integrated with a module to control the imposition of turns on the filament.

Example 1

Capillary Tube Preparation

Capillary tubes 123, 2×0.2 mm ID (Vitrocom, Mountain Lake, N.J., USA) previously piranha cleaned, were incubated 8 hrs in anti-digoxigenin solution (PBS complemented with 0.2 mg/ml polyclonal anti-Digoxigenin, Roche, Indianapolis, Ind., USA) and 12 hrs in blocking solution (10 mM phosphate buffer complemented with 10 mg/ml acetylated BSA, Sigma, St Louis, Mo., USA; 0.1% Tween-20; 10 mM EDTA; 3 mM $NaN_3$). Both incubations were performed at 37° C., and capillary tubes stored at 4° C.

The substrate 101 can be coated with a material other than anti-digoxigenin. One of skill in the art will select an appropriate coating material based on the material of which the substrate 101 is formed and the filament 105 to be examined, as well as other experimental considerations.

Example 2

Nanorod Synthesis

Nanorods 121 were prepared by electrodeposition into the 200 nm diameter pores of an aluminum oxide template membrane (Whatman, Springfield Mill, Kent, England).[23,28] An 800 nm cooper film was evaporated onto one side of a membrane and used as the working electrode. The nanorods 121 were formed by filling the pores of the membrane by the deposited material. Three different metal segments were deposited by changing the electrolytic solution. An 8 µm copper sacrificial segment was deposited from 500 mM $CuSO_4$ (pH=1.0) by running a charge of 7 coulombs at −160 mV. The platinum segment 1003 was produced by running a charge of 3 coulombs from a solution of 17 mM $(NH_4)_2PtCl_6$ and 250 mM $Na_2HPO_4$ (pH=7.8) at −350 mV, producing a 1.7±0.4 µm long segment. Finally, the nickel segment 1001 was deposited from a solution of 500 mM $NiSO_4$ and 670 mM boric acid (pH=3.8) by running 0.4 coulombs at −800 mV, producing a 0.09±0.03 µm long segment. Copper was etched in a copper etchant BTP bath (Transene, Danvers, Mass., USA) at 40° C. for 12 hrs, and $Al_2O_3$ was etched in a 2 M KOH bath at 65° C. for 8 hrs.

FIG. 10 presents aspects of Ni—Pt nanorod 121 fabrication. FIG. 10a shows a scanning electron micrograph of the aluminum oxide template (Whatman, Springfield Mill, Kent, UK) used for nanorod electrodeposition. The electrodeposition took place in the capillary pores of the template, which had a diameter of 200 nm (image bar=1 µm). FIG. 10b shows a scanning electron micrograph of a Ni—Pt nanorod 121 (image bar=0.5 µm). The Pt 1003 and Ni 1001 segments were sequentially electrodeposited using electrolytic solutions containing ammonium chloroplatinate and nickel sulfate, respectively. The length of each segment was controlled by the total electric charge circulated through the electrochemical cell at each deposition stage. After deposition, the aluminum oxide template was etched to liberate the nanorods (see Materials section).

Example 3

Nanorod Functionalization

Nanorods 121 were functionalized by incubating them for 30 min in a 10 mM phosphate buffer complemented with 0.1 mg/ml Neutravidin tetramethylrhodamine conjugate (Invitrogen, Eugene, Oreg., USA) and 0.1% Tween-20. Shaking during the incubation prevented aggregation of nanorods 121. Treatment with rhodamine-labeled Neutravidin allowed the visualization of the nanorods 121 (FIG. 14).

Figure 14:
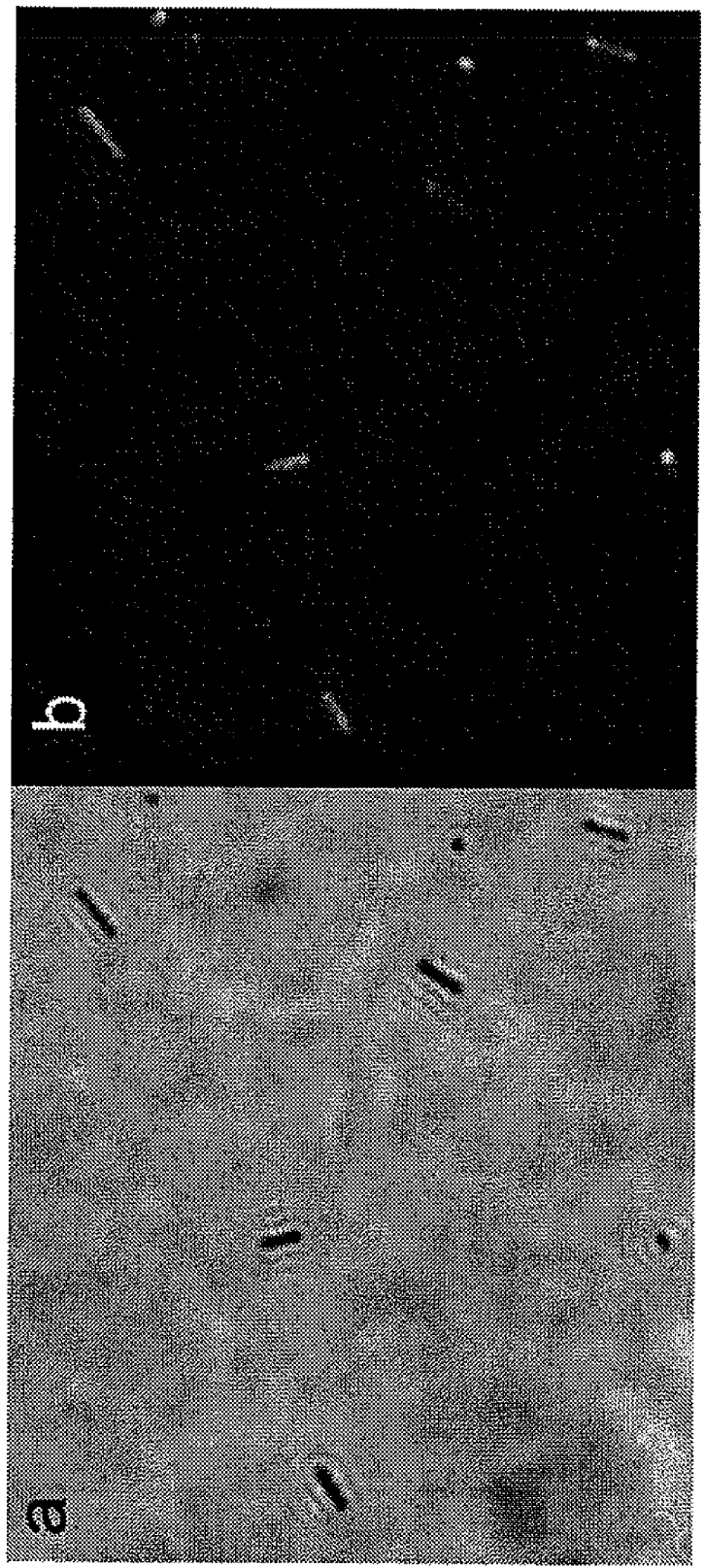
FIG. 14a-14b shows Ni—Pt nanorods coated with tetramethylrhodamine conjugated Neutravidin.

FIG. 14 shows the Ni—Pt nanorods 121 coated with tetramethylrhodamine conjugated Neutravidin. The same field of nanorods 121 visualized using FIG. 14a bright field and FIG. 14b fluorescence, showing the Neutravidin bound to the nanorod surface.

We tested the quality of Neutravidin coating by measuring the percentage of nanorods 121 that were able to introduce supercoils into the bound DNA molecule. We found that there were always some molecules in which rotation of the handle did not result in molecule shortening. This behavior can result from single attachment points around which the molecule can swivel, releasing the twists. Such attachments can result from nicks in the DNA, or due to single connections with the probe or the glass: if DNA is linked to one of the surfaces by just one biotin or digoxigenin link, then it can swivel around that link. We found that our Neutravidin-labeled nanorods 121 gave the same percentage of supercoiled DNA (~70%) as commercially available Streptavidin-coated beads (Invitrogen), indicating that the surface density of Neutravidin nanorods was not a limiting factor.

Alternatively, a compound other than Neutravidin can be used to coat the nanorods 121 and/or magnetic probes 109. One of skill in the art will be able to select an appropriate coating material depending on the filament 105 to be examined and other experimental considerations.

Example 4

DNA Bi-Functionalization

We used the same DNA fragment for naked DNA and chromatin experiments. The DNA fragment was generated from ligation of three pieces: two 900 bp DNA fragments, produced by PCR, containing either biotin- or digoxigenin-labeled nucleotides; and a central 10 kb fragment containing a 35×208 basepair (bp) repeat tandem array of the 5S positioning sequence flanked by vector DNA (a gift of Jeffrey Hansen). To enrich the desired population of DNA constructs (the 10 kb fragment flanked by both biotin- and digoxigenin-labeled fragments), we employed restriction enzymes to yield compatible cohesive ends: the biotin- and digoxigenin-labeled fragments were digested with Nhe I, and the vector containing the central array was digested with Xba I. Ligation of these fragments was performed in the presence of the Xba I and Nhe I restriction enzymes, and the correct product was therefore not recleavable by these enzymes. Compounds other than biotin and/or digoxigenin can be used to label a filament 105 and attach the filament 105 to the magnetic probe 109 and the substrate 101. One of skill in the art will be able to select appropriate compound(s) for labeling the filament 105 based on the filament 105 to be investigated, the materials of which the magnetic probe 105 and the substrate 101 are formed, and other experimental considerations.

Example 5

Chromatin Preparation

Wildtype histones H2A, H2B, H3, and H4 from *Xenopus laevis* were expressed, purified, and reconstituted into octamers.[29] Chromatin was generated by depositing these histone octamers onto the functionalized DNA using the salt gradient dialysis technique.[29] For the reconstitution, the ratio of DNA to histones was varied from 0.6:1 to 1.2:1. We examine the level of histone saturation using analytical ultracentrifugation.[30,31] For the histone:DNA ratios of 1.0:1.0 and lower, the samples appear relatively homogeneous, with 80% of each sample sedimenting at 23 S (0.6:1 ratio), 47 S (0.8:1 ratio), 72 S (1.0:1 ratio). In contrast, the 1.2:1 ratio displayed aberrant sedimentation that precludes van Holde/Weischet analysis, and is likely due to oversaturation of the array (data not shown). Chromatin samples prepared at a histone:DNA ratios of 0.8:1.0 were used for magnetic tweezer manipulation. Individual fibers 105 differed significantly in the apparent number of nucleosomes (see FIG. 5a). A similar heterogeneity was also observed by Bancaud et al.[8]

Example 6

Probe Assembly

Solutions were introduced into a capillary tube 123 by filling a pipet tip attached to the capillary via tygon tubing, and then pulling the solution into the capillary tube with a syringe pump (Harvard Apparatus, 11 Plus, Holliston, Mass., US). During the experiment, the connecting tygon tubing was clamped off to isolate the system from the exterior. All the experiments were conducted in standard buffer (10 mM phosphate buffer with 0.1% Tween-20). Naked DNA molecules or chromatin fibers (50 ng/ml) 105 were incubated in the capillary tube for 10 min to allow digoxigenin-labeled DNA ends to interact with the anti-digoxigenin coated glass surface. Unbound DNA or chromatin was washed away by flowing 300 µl of standard buffer through the capillary 123. Finally, 1 µm diameter superparamagnetic beads 119 (Dynabeads MyOne, Tosylactivated, Invitrogen, Carlsbad, Calif., USA) and functionalized nanorods 121 were flowed into the capillary. The surface of the beads 119 was not activated. Beads 119 and nanorods 121 self assemble in the absence of an external magnetic field, by the attraction between the ferromagnetic Ni segment and the superparamagnetic bead 119. During assembly, the preferred dipole orientation of the bead 119 aligns with the Ni segment dipole, such that under the vertical magnetic field created by the cylindrical magnet, the dipole of the bead 119 and the dipole of the Ni segment 1001 are vertical while the axis of the nanorod 121 is horizontal. The probes were lifted by placing the capillary tube under the cylindrical magnet 107 which was held by a linear stage (460P-XYZ, Newport, Irvine, Calif., US) ~2 mm above the capillary tube 123.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES (1) Peter, B. J.; Arsuaga, J.; Breier, A. M.; Khodursky, A. B.; Brown, P. O.; Cozzarelli, N. R. *Genome Biology* 2004, 5,
(2) Koster, D. A.; Croquette, V.; Dekker, C.; Shuman, S.; Dekker, N. H. *Nature* 2005, 434, 671-674
(3) Metzler, R.; Ambjornsson, T.; Hanker, A.; Zhang, Y. L.; Levene, S. *Computational and Theoretical Nanoscience* 2007, 4, 1-49
(4) Kouzine, F.; Sanford, S.; Elisha-Feil, Z.; Levens, D. *Nature Structural & Molecular Biology* 2008, 15, 146-154
(5) Liu, L. F.; Wang, J. C. *Proc Natl Acad Sci USA* 1987, 84, 7024-7
(6) Koster, D. A.; Palle, K.; Bot, E. S.; Bjornsti, M. A.; Dekker, N. H. *Nature* 2007, 448, 213-7
(7) Pomerantz, R. T.; Ramjit, R.; Gueroui, Z.; Place, C.; Anikin, M.; Leuba, S.; Zlatanova, J.; McAllister, W. T. *Nano Letters* 2005, 5, 1698-1703
(8) Bancaud, A.; Silva, N. C. E.; Barbi, M.; Wagner, G.; Allemand, J. F.; Mozziconacci, J.; Lavelle, C.; Croquette, V.; Victor, J. M.; Prunell, A.; Viovy, J. L. *Nature Structural & Molecular Biology* 2006, 13, 444-450
(9) Forth, S.; Deufel, C.; Sheinin, M. Y.; Daniels, B.; Sethna, J. P.; Wang, M. D. *Physical Review Letters* 2008, 100,
(10) Deufel, C.; Forth, S.; Simmons, C. R.; Dejgosha, S.; Wang, M. D. *Nature Methods* 2007, 4, 223-225
(11) Oroszi, L.; Galajda, P.; Kirei, H.; Bottka, S.; Ormos, P. *Physical Review Letters* 2006, 97,
(12) Bryant, Z.; Stone, M. D.; Gore, J.; Smith, S. B.; Cozzarelli, N. R.; Bustamante, C. *Nature* 2003, 424, 338-341
(13) Strick, T. R.; Allemand, J. F.; Bensimon, D.; Bensimon, A.; Croquette, V. *Science* 1996, 271, 1835-1837
(14) Haber, C.; Wirtz, D. *Review of Scientific Instruments* 2000, 71, 4561-4570
(15) Leuba, S. H.; Karymov, M. A.; Tomschik, M.; Ramjit, R.; Smith, P.; Zlatanova, J. *Proceedings of the National Academy of Sciences of the United States of America* 2003, 100, 495-500
(16) Bancaud, A.; Wagner, G.; Conde e Silva, N.; Lavelle, C.; Wong, H.; Mozziconacci, J.; Barbi, M.; Sivolob, A.; Le Cam, E.; Mouawad, L.; Viovy, J. L.; Victor, J. M.; Prunell, A. *Molecular Cell* 2007, 27, 135-147
(17) Yan, J.; Maresca, T. J.; Skoko, D.; Adams, C. D.; Xiao, B.; Christensen, M. O.; Heald, R.; Marko, J. F. *Mol Biol Cell* 2007, 18, 464-74
(18) Charvin, G.; Strick, T. R.; Bensimon, D.; Croquette, V. *Annual Review of Biophysics and Biomolecular Structure* 2005, 34, 201-219
(19) Gore, J.; Bryant, Z.; Stone, M. D.; Nollmann, M. N.; Cozzarelli, N. R.; Bustamante, C. *Nature* 2006, 439, 100-104
(20) Revyakin, A.; Ebright, R. H.; Strick, T. R. *Proceedings of the National Academy of Sciences of the United States of America* 2004, 101, 4776-4780
(21) Revyakin, A.; Liu, C. Y.; Ebright, R. H.; Strick, T. R. *Science* 2006, 314, 1139-1143
(22) Lia, G.; Semsey, S.; Lewis, D. E.; Adhya, S.; Bensimon, D.; Dunlap, D.; Finzi, L. *Nucleic Acids Res* 2008, 36, 4204-10
(23) Whitney, T. M.; Jiang, J. S.; Searson, P. C.; Chien, C. L. *Science* 1993, 261, 1316-1319
(24) Gosse, C.; Croquette, V. *Biophysical Journal* 2002, 82, 3314-3329
(25) Chen, M.; Chien, C. L.; Searson, P. C. *Chemistry of Materials* 2006, 18, 1595-1601
(26) Marko, J. F. *Physical Review E* 2007, 76,
(27) Strick, T. R.; Allemand, J. F.; Bensimon, D.; Croquette, V. *Biophysical Journal* 1998, 74, 2016-2028

We claim:

1. A system for determining torque applied to a filament, comprising:
   a substrate having a first binding point suitable for attachment of a first end of a filament;

a magnet arranged in a relationship opposed to the substrate;

a magnetic probe having a magnetic moment, an azimuthal orientation, and a second binding point suitable for attachment of a second end of the filament, positioned between the substrate and the magnet; and a translation stage disposed proximate to the substrate and the magnet;

an imaging device proximate to the substrate, magnet, and magnetic probe;

wherein the imaging device is adapted to determine the azimuthal orientation of the magnetic probe, and wherein the second binding point of the magnetic probe is offset from the magnetic moment.

2. The system of claim 1, wherein the translation stage is attached to the substrate.

3. The system of claim 1, wherein the translation stage is attached to the magnet.

4. The system of claim 1, wherein the magnetic moment of the magnetic probe is approximately parallel to an orientation axis passing through the first binding point and the second binding point.

5. The system of claim 1, wherein the translation stage has two axes of motion.

6. The system of claim 1,
wherein the magnet is a single permanent magnet.

7. The system of claim 6,
wherein the single permanent magnet is affixed to a z-stage translatable in a direction approximately parallel to an orientation axis passing through the first binding point and the second binding point.

8. The system of claim 1,
wherein the magnet is an electromagnet.

9. The system of claim 8, wherein a magnetic field of the electromagnet is variable.

10. The system of claim 1,
wherein the magnetic probe comprises a magnetic bead and a lever,
wherein the magnetic moment of the magnetic probe passes through the magnetic bead, and
wherein the lever comprises the second binding point.

11. The system of claim 1,
wherein the magnetic probe comprises a superparamagnetic material.

12. The system of claim 1, wherein the filament is a macromolecule.

13. A method for determining the torque applied to a filament, comprising:
affixing a first end of the filament to a substrate;
affixing a second end of the filament to a magnetic probe having an azimuthal orientation;
applying an external magnetic field having a magnetic axis to move the magnetic probe and elongate the filament along an orientation axis passing through the first end and the second end of the filament;
moving the first end of the filament relative to the magnetic axis of the external magnetic field to change the azimuthal orientation of the magnetic probe and impose twist on the filament;
obtaining images of the magnetic probe at a plurality of successive times;
using the images to determine the azimuthal orientation of the magnetic probe at the successive times;
obtaining a probability distribution of azimuthal orientations from the azimuthal orientations at the successive times; and
determining the torque on the filament from the probability distribution of azimuthal orientations.

14. The method of claim 13, wherein the filament is a polynucleotide.

15. The method of claim 13, wherein the first end of the filament is moved relative to the magnetic axis by translating the substrate.

16. The method of claim 15, wherein the substrate is translated in a curve having a winding number about the magnetic probe.

17. The method of claim 16, wherein the winding number is at least one.

18. The method of claim 16, further comprising determining the torque on the filament as a function of the azimuthal orientation and/or the winding number.

19. The method of claim 16, further comprising varying the external magnetic field to vary an elongation force along the orientation axis of the filament.

20. The method of claim 19, further comprising determining the torque as a function of the elongation force and the azimuthal orientation and/or the winding number.

21. The method of claim 13, wherein the first end of the filament is moved relative to the magnetic axis by translating the external magnetic field.

* * * * *